United States Patent
Bikhchandani et al.

(10) Patent No.: US 12,059,268 B1
(45) Date of Patent: *Aug. 13, 2024

(54) MANAGING MEAL EXCURSIONS IN BLOOD GLUCOSE DATA

(71) Applicant: Verily Life Sciences LLC, Mountain View, CA (US)

(72) Inventors: Nikhil Bikhchandani, San Francisco, CA (US); Howard Zisser, Santa Barbara, CA (US); Joshua Burkart, Boston, MA (US); Shih-Yo Cheng, Milpitas, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 243 days.

This patent is subject to a terminal disclaimer.

(21) Appl. No.: 17/521,074

(22) Filed: Nov. 8, 2021

Related U.S. Application Data

(63) Continuation of application No. 16/399,170, filed on Apr. 30, 2019, now Pat. No. 11,166,670.

(51) Int. Cl.
*G16H 20/17* (2018.01)
*A61B 5/00* (2006.01)
(Continued)

(52) U.S. Cl.
CPC ........ *A61B 5/4866* (2013.01); *A61B 5/14532* (2013.01); *A61B 5/7267* (2013.01); *A61B 5/7282* (2013.01); *G16H 50/20* (2018.01)

(58) Field of Classification Search
CPC . A61B 5/4866; A61B 5/14532; A61B 5/7267; A61B 5/7282; G16H 50/20
See application file for complete search history.

(56) References Cited

U.S. PATENT DOCUMENTS 6,553,386 B1 4/2003 Alabaster
8,249,946 B2 8/2012 Froseth et al.
(Continued)

OTHER PUBLICATIONS

Albers, David J., et al., "Personalized glucose forecasting for type 2 diabetes using data assimilation", "Personalized glucose forecasting for type 2 diabetes using data assimilation;" PLoS Comput Biol 13(4): e1005232. https://doi.org/10.1371/journal.pcbi.1005232; Apr. 27, 2017; 1-38.

(Continued)

*Primary Examiner* — Maroun P Kanaan
(74) *Attorney, Agent, or Firm* — Perkins Coie LLP

(57) ABSTRACT

To better understand the impact that meals have on the blood glucose level, some individuals with diabetes have begun recording meals consumed over time. However, the relationship between meals consumed by an individual and the glycemic health state of the individual has been difficult to understand. Introduced here are computer programs and associated computer-implemented techniques for utilizing information regarding the meals consumed by an individual to manage the blood glucose level of the individual in a personalized manner. By consistently and properly attributing physiological responses represented as excursions in blood glucose measurements to meals, the relationship between these meals and the glycemic health state can be better understood. For example, by examining this relationship, a diabetes management platform may be able to identify appropriate recommendations for monitoring, managing, and/or improving the glycemic health state of an individual.

25 Claims, 16 Drawing Sheets

(51) Int. Cl.
  *A61B 5/145* (2006.01)
  *G16H 50/20* (2018.01)

(56) References Cited

U.S. PATENT DOCUMENTS

| | | | |
|---|---|---|---|
| 8,597,570 | B2 | 12/2013 | Terashima et al. |
| 10,624,591 | B1* | 4/2020 | Biesinger ............... G16H 10/60 |
| 2002/0032583 | A1 | 3/2002 | Joao |
| 2005/0027182 | A1 | 2/2005 | Siddiqui et al. |
| 2005/0038332 | A1 | 2/2005 | Saidara et al. |
| 2008/0154513 | A1 | 6/2008 | Kovatchev et al. |
| 2008/0201169 | A1 | 8/2008 | Galasso et al. |
| 2008/0208027 | A1 | 8/2008 | Heaton |
| 2008/0255438 | A1 | 10/2008 | Saidara et al. |
| 2009/0105568 | A1 | 4/2009 | Bugler |
| 2009/0177068 | A1 | 7/2009 | Stivoric et al. |
| 2013/0325504 | A1 | 12/2013 | Greene et al. |
| 2014/0128705 | A1 | 5/2014 | Mazlish |
| 2015/0045641 | A1 | 2/2015 | Rule |
| 2015/0141770 | A1 | 5/2015 | Rastogi et al. |
| 2015/0289823 | A1 | 10/2015 | Rack-Gomer et al. |
| 2016/0378937 | A1 | 12/2016 | Soni et al. |
| 2017/0128007 | A1* | 5/2017 | Hayter ............... G09B 5/02 |
| 2017/0185748 | A1 | 6/2017 | Budiman et al. |
| 2017/0220751 | A1 | 8/2017 | Davis et al. |
| 2017/0308981 | A1 | 10/2017 | Razavian et al. |
| 2018/0197628 | A1 | 7/2018 | Wei et al. |
| 2019/0175079 | A1 | 6/2019 | Nishida et al. |
| 2019/0175080 | A1 | 6/2019 | Varsavsky et al. |
| 2019/0290172 | A1 | 9/2019 | Hadad et al. |

OTHER PUBLICATIONS

Lim, Teck-Onn, et al., "Bimodality in Blood Glucose Distribution", "Bimodality in Blood Glucose Distribution; Is it universal?"; Clinical Research Centre, the Department of Nephrology, and the Public Health Institute, Kuala Lumpur, Malaysia; Apr. 10, 2002; pp. 2212-2217.

Vittinghoff, Eric, et al., "Regression Methods in Biostatistics", Regression Methods in Biostatistics: Linear, Logistic, Survival, and Repeated Measures Models; ISBN 0-387-20275-7; San Francisco, CA; Oct. 2004; 346 pages.

* cited by examiner

1300

1301
Receive a series of blood glucose values associated with an individual

1302
Examine the series of blood glucose values to detect an excursion in the blood glucose level 1303
Acquire meal data associated with meal(s) consumed by the individual 1304
Match the excursion to a particular meal of the meal(s)

1305
Determine that the excursion occurred in response to a meal that negatively affected the glycemic health state 1306
Identify the excursion as representative of a negative event

Acquire a series of labeled excursions corresponding to a series of events

1402

Train a supervised model with the series of labeled excursions

1403

Receive a series of blood glucose values associated with a subject

1404

Apply the supervised model to the series of blood glucose values

1405

Produce a summary of excursions, if any, classified as being indicative of negative events likely to negatively affect the health of the subject

1406

Post the summary to an interface for review by an individual

1407

Apply an unsupervised model to another series of excursions to produce cluster(s)

1408

Acquire images of meals that correspond to the other series of excursions

1409

Sort the images into batch(es) corresponding to the cluster(s) formed by the unsupervised model

Identify a series of historical meals consumed by an individual whose glycemic health state is to be monitored

1502

Detect multiple excursions in a series of blood glucose values associated with the individual

1503

Match each excursion with a corresponding historical meal

1504

Classify, based on the corresponding excursion, each historical meal as a negative meal, a positive meal, or a neutral meal

1505

Identify a meal preference of the individual by examining pixel data of images of the series of historical meals

1506

Generate a meal recommendation based on the meal preference

FIGURE 15

MANAGING MEAL EXCURSIONS IN BLOOD GLUCOSE DATA

CROSS-REFERENCE TO RELATED APPLICATIONS

This application is a continuation of U.S. patent application Ser. No. 16/399,170, titled "Managing Meal Excursions in Blood Glucose Data" and filed on Apr. 30, 2019, which is incorporated by reference herein in its entirety.

TECHNICAL FIELD

Various embodiments concern computer programs and associated computer-implemented techniques for utilizing information regarding the meals consumed by individuals to manage the blood glucose levels of those individuals.

BACKGROUND

After ingestion of a foodstuff that contains carbohydrates, the human body breaks down the carbohydrates into glucose, which serves as a source of energy for the cells of the human body. Glucose is transported via circulation within the blood stream. Therefore, ingestion of foodstuffs will influence the concentration of glucose within the blood stream (also referred to as the "blood glucose level" or "glucose level").

According to the American Diabetes Association (ADA), a normal blood glucose level for people without diabetes is below 6.9 mmol/L (125 mg/dL). Meanwhile, the target blood glucose range for people with diabetes is 5.0-7.2 mmol/L (90-130 mg/dL) before meals and less than 10 mmol/L (180 mg/dL) after meals. However, some people with diabetes struggle to consistently stay within the recommended range.

BRIEF DESCRIPTION OF THE DRAWINGS

Various features of the technology will become more apparent to those skilled in the art from a study of the Detailed Description in conjunction with the drawings. Embodiments of the technology are illustrated by way of example and not limitation in the drawings, in which like references may indicate similar elements.

FIG. 13 depicts a flow diagram of a process for matching excursions discovered in physiological data to meals consumed by an individual.

FIG. 14 depicts a flow diagram of a process for determining whether to classify excursions as events that increase health risk.

FIG. 15 depicts a flow diagram of a process for managing the glycemic health state of an individual in a personalized manner based on the meals consumed by the individual.

Figure 1:
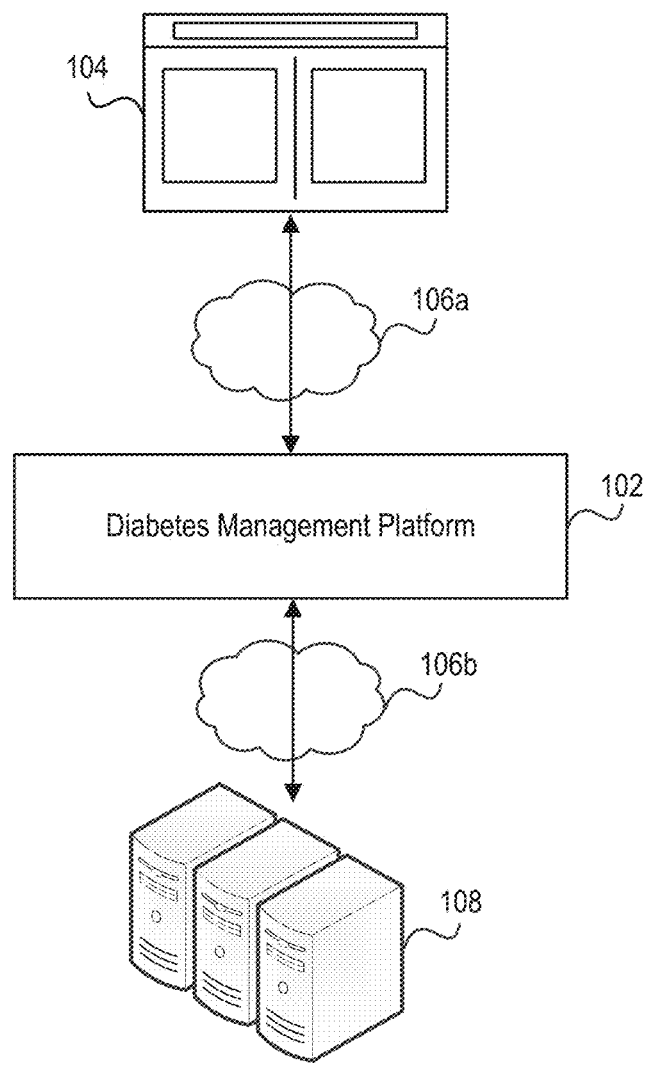
FIG. 1 illustrates a network environment that includes a diabetes management platform.

The drawings depict various embodiments for the purpose of illustration only. Those skilled in the art will recognize that alternative embodiments may be employed without departing from the principles of the technology. Accordingly, while specific embodiments are shown in the drawings, the technology is amenable to various modifications.

DETAILED DESCRIPTION

Diabetes mellitus (commonly referred to as "diabetes") is a group of metabolic disorders in which the affected individuals experience high blood glucose levels over a prolonged period. If left untreated, diabetes can cause many complications. For example, long-term complications can include cardiovascular disease, stroke, chronic kidney disease, foot ulcers, and eye damage.

Blood glucose monitoring is the process through which the concentration of glucose within the blood stream (also referred to as the "blood glucose level" or "glucose level") is tested. A test is typically performed by piercing the skin to draw blood, and then applying the blood to a disposable, chemically-active test strip. Historically, an individual with diabetes would take several measurements throughout the day in an ad hoc manner using a blood glucose meter. Because blood glucose meters require that individuals manually perform each test, measurements are often generated sporadically. However, it can be difficult to establish the blood glucose level between these discrete measurements.

Continuous glucose monitoring represents a promising new way for individuals to gain insights into the diabetes disease state. In contrast to a blood glucose meter, a continuous glucose monitor can continually monitor the blood glucose level throughout the day. For example, a continuous glucose monitor may automatically take blood glucose measurements every five minutes, ten minutes, etc.

By taking measurements more frequently, individuals with diabetes can form a better understanding of how their blood glucose level fluctuates throughout the day. However, it can be difficult to understand which activities (also referred to as "glycemic events") have the largest impact on the glycemic health state, either in the short term or the long term, regardless of how frequently measurements are taken. One example of a glycemic event is a foodstuff consumption event (also referred to as a "meal" or a "meal event").

To better understand the impact that meals have on the blood glucose level, some individuals with diabetes have begun recording meals consumed over time. For example, an individual may separately log each meal by capturing an image of the meal, labeling the foodstuff(s) included in the meal, etc. However, the relationship between meals consumed by an individual and the glycemic health state of the individual has been difficult to understand.

Introduced here, therefore, are computer programs and associated computer-implemented techniques for utilizing information regarding the meals consumed by an individual to manage the blood glucose level of the individual. Because the technology described herein enables physiological responses represented as excursions in blood glucose measurements to be consistently and properly attributed to meals, the relationship between these meals and the glycemic health state can be better understood. Understanding this relationship may be critical to identifying appropriate recommendations for monitoring, managing, and/or improving the glycemic health state.

Initially, a diabetes management platform can acquire a series of blood glucose measurements associated with an individual (also referred to as a "subject" or a "patient"). This series of blood glucose measurements may also be referred to as "physiological data." As further described below, the physiological data can include explicit data values (also referred to as "explicit measurements"), implicit data values (also referred to as "implicit measurements"), or any combination thereof. For example, the physiological data could include implicit data values interspersed between explicit data values generated by a blood glucose meter. As another example, physiological data could include explicit data values generated by a continuous glucose monitor followed by implicit data values representative of estimated blood glucose measurements during a future time interval.

The diabetes management platform can then parse the physiological data to discover excursions in the blood glucose level that are related to the consumption of a meal. Each excursion corresponds to a signal feature defined by one or more data values. The diabetes management platform can discover excursions in several different ways. For example, the diabetes management platform can identify excursions by applying processing algorithm(s) to identify data value(s) that match a pattern in accordance with a pattern-defining parameter. As another example, the diabetes management platform can train a classification model to identify the data value(s) responsive to a determination that a matching window of physiological data corresponds to a meal.

Moreover, the diabetes management platform can acquire meal data associated with meals consumed by the individual. Generally, at least some of the meal data is reported by the individual. For example, the meal data may include images of meals that have been consumed by the individual. In some embodiments these images are captured in conjunction with reporting the consumption of a meal (e.g., by initiating a mobile application on a mobile phone that permits images to be captured), while in other embodiments these images are attached/identified as part of the reporting (e.g., by selecting the images from a library of images hosted on a mobile phone). As another example, the meal data may include information provided by the individual regarding each meal, such as the foodstuff(s) included in the meal, the name of a restaurant, the location of the meal, the time of the meal, etc. In some embodiments, however, at least some of the meal data is automatically derived on behalf of the individual. For example, the diabetes management platform may establish the time of a meal by examining metadata associated with an image of the meal that has been uploaded by the individual. As another example, the diabetes management platform may infer the location of a meal based on the location of a computing device (e.g., as determined by its operating system) proximate to the time of the meal.

The diabetes management platform can match excursions discovered in the physiological data to meals consumed by the individual. Such action enables the diabetes management platform to better understand how meals affect the glycemic health state of the individual, both in the short term and the long term. For example, in some embodiments, the diabetes management platform is configured to determine whether each excursion should be classified as being indicative of a negative event likely to negatively affect the glycemic health of the individual, a positive event likely to positively affect the glycemic health of the individual, or a neutral event that is unlikely to affect the glycemic health of the individual. By classifying excursions over an extended duration (e.g., several days, weeks, or months), the diabetes management platform can determine meal preferences of the individual, discover which meals increase the likelihood of experiencing an adverse health-related event such as diabetic ketoacidosis, and identify appropriate recommendations for improving the glycemic health state of the individual.

Embodiments may be described with reference to particular computer programs, system configurations, networks, etc. However, those skilled in the art will recognize that these features are equally applicable to other computer program types, system configurations, network types, etc. Moreover, the technology can be embodied using special-purpose hardware (e.g., circuitry), programmable circuitry appropriately programmed with software and/or firmware, or a combination of special-purpose hardware and programmable circuitry. Accordingly, embodiments may include a machine-readable medium having instructions that may be used to program a computing device to perform a process for examining physiological data comprising explicit data values and/or implicit data values, discovering excursions in the physiological data, matching the excursions to meals consumed by an individual, clustering the meals based on excursion similarity, identifying a recommendation for improving the glycemic health state based on the meal clusters, etc.

Terminology

References in this description to "an embodiment" or "one embodiment" means that the particular feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the words "comprise" and "comprising" are to be construed in an inclusive sense rather than an exclusive or exhaustive sense (i.e., in the sense of "including but not limited to"). The terms "connected," "coupled," or any variant thereof is intended to include any connection or coupling between two or more elements, either direct or indirect. The coupling/connection can be physical, logical, or a combination thereof. For example, devices may be electrically or communicatively coupled to one another despite not sharing a physical connection.

The term "based on" is also to be construed in an inclusive sense rather than an exclusive or exhaustive sense. Thus, unless otherwise noted, the term "based on" is intended to mean "based at least in part on."

The term "module" refers broadly to software components, hardware components, and/or firmware components. Modules are typically functional components that can generate useful data or other output(s) based on specified input(s). A module may be self-contained. A computer program may include one or more modules. Thus, a computer program may include multiple modules responsible for completing different tasks or a single module responsible for completing all tasks.

When used in reference to a list of multiple items, the word "or" is intended to cover all of the following interpretations: any of the items in the list, all of the items in the list, and any combination of items in the list.

The sequences of steps performed in any of the processes described here are exemplary. However, unless contrary to physical possibility, the steps may be performed in various sequences and combinations. For example, steps could be added to, or removed from, the processes described here. Similarly, steps could be replaced or reordered. Thus, descriptions of any processes are intended to be open-ended.

Technology Overview

FIG. 1 illustrates a network environment 100 that includes a diabetes management platform 102. Individuals can interface with the diabetes management platform 102 via an interface 104. The diabetes management platform 102 may be responsible for parsing physiological data pertaining to an individual to discover excursions in the blood glucose level, examining meal data to discover meals that have been consumed by the individual, matching the excursions to the meals, clustering the meals based on similarity of the corresponding excursions, providing a meal recommendation for improving the glycemic health state of the individual based on the meal clusters, etc. The diabetes management platform 102 may also be responsible for creating interfaces through which the individual can view physiological data, manage preferences, etc.

Physiological data could specify the blood glucose level of the individual accessing the interface 104 or some other person. For example, in some embodiments the interface 104 enables a person with diabetes to view their own physiological data, while in other embodiments the interface 104 enables an individual to view physiological data associated with some other person. The individual may be a health coach responsible for monitoring the glycemic health of the other person. Examples of health coaches include medical professionals (e.g., a physician or nurse), diabetic health counselors, family members of the other person, etc. As further described below, the physiological data may include explicit data values (e.g., those generated by a glucose monitoring device, such as a blood glucose meter or a continuous glucose monitor) and/or imputed data values (e.g., those generated by the diabetes management platform 102 based on past explicit data values). Some interfaces are configured to facilitate interactions between subjects and health coaches, while other interfaces are configured to serve as informative dashboards for subjects.

As noted above, the diabetes management platform 102 may reside in a network environment 100. Thus, the diabetes management platform 102 may be connected to one or more networks 106a-b. The network(s) 106a-b can include personal area networks (PANs), local area networks (LANs), wide area networks (WANs), metropolitan area networks (MANs), cellular networks, the Internet, etc. Additionally or alternatively, the diabetes management platform 102 can be communicatively coupled to computing device(s) over a short-range communication protocol, such as Bluetooth® or Near Field Communication (NFC).

The interface 104 is preferably accessible via some combination of a web browser, desktop application, mobile application, or over-the-top (OTT) application. Accordingly, the interface 104 may be viewed on a personal computer, tablet computer, personal digital assistant (PDA), mobile phone, game console, music player, wearable electronic device (e.g., a watch or fitness accessory), network-connected ("smart") electronic device, (e.g., a television or home assistant device), virtual/augmented reality system (e.g., a head-mounted display), or some other electronic device.

Some embodiments of the diabetes management platform 102 are hosted locally. That is, the diabetes management platform 102 may reside on the computing device used to access the interface 104. For example, the diabetes management platform 102 may be embodied as a mobile application executing on a mobile phone. Other embodiments of the diabetes management platform 102 are executed by a cloud computing service operated by Amazon Web Services® (AWS), Google Cloud Platform™, Microsoft Azure®, or a similar technology. In such embodiments, the diabetes management platform 102 may reside on a host computer server that is communicatively coupled to one or more content computer servers 108. The content computer server(s) 108 can include different types of data (e.g., physiological data and/or meal data), user information (e.g., profiles, credentials, and health-related information such as age, diabetes classification, etc.), and other assets. Such information could also be stored on the host computer server.

Certain embodiments are described in the context of network-accessible interfaces. However, those skilled in the art will recognize that the interfaces need not necessarily be accessible via a network. For example, a computing device may be configured to execute a self-contained computer program that does not require network access. Instead, the self-contained computer program may cause necessary assets (e.g., physiological data, meal data, and processing operations) to be downloaded at a single point in time or on a periodic basis (e.g., weekly, daily, or hourly).

Figure 2:
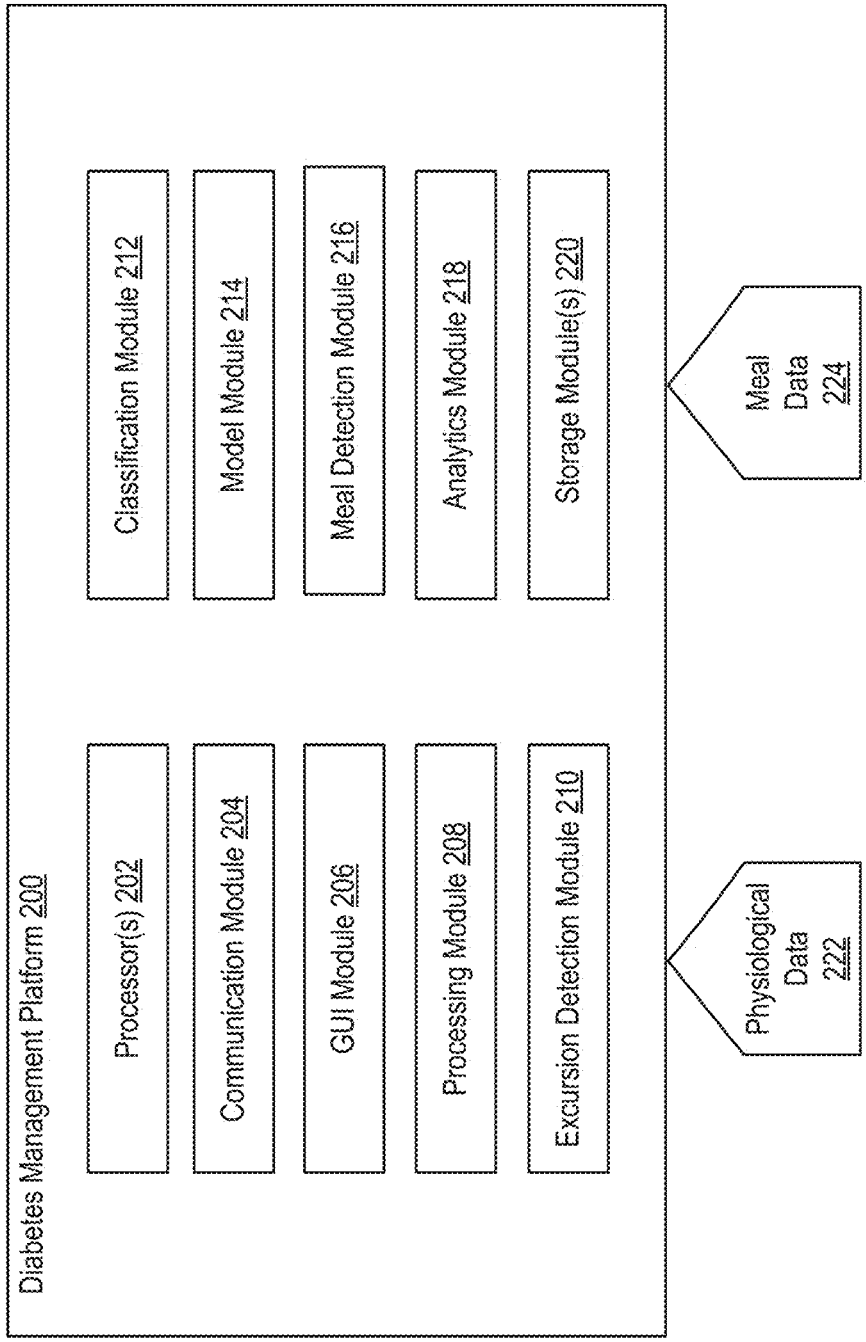
FIG. 2 depicts the high-level architecture of a diabetes management platform able to analyze physiological data to detect excursions in the blood glucose level of a subject, analyze meal data to detect meals that have been consumed by the subject, and then match the excursions in the blood glucose level to the meals.

FIG. 2 depicts the high-level architecture of a diabetes management platform 200 able to analyze physiological data 222 to detect excursions in the blood glucose level of a subject, analyze meal data 224 to detect meals that have been consumed by the subject, and then match the excursions in the blood glucose level to the meals. Said another way, the diabetes management platform 200 may correlate each excursion in the blood glucose level with a meal consumed by the subject. In some embodiments, the diabetes management platform 200 is able to provide recommendations based on an analysis of the meals and the resulting excursions in the blood glucose level. For example, upon discovering an excursion that indicates a meal has negatively affected the glycemic health of the subject, the diabetes management platform 200 may recommend that the subject refrain from consuming the meal (or similar meals) in the future.

As further described below, the physiological data 222 can include explicit data values and/or imputed data values. Accordingly, the excursions detected by the diabetes management platform 200 may be actual excursions (e.g., as discovered in a real-time stream of explicit data values) or predicted excursions (e.g., as discovered in a real-time stream of imputed data values). In some embodiments the imputed data values reside between explicit data values (e.g., if a subject sporadically measures the blood glucose level using a blood glucose meter), while in other embodiments the imputed data values reside in a future time interval for which there are no explicit data values. Thus, imputed data values can be applied to a personalized statistical model to generate additional data points in between explicit data values. In such embodiments, the personalized statistical model can be trained on historical explicit data values (e.g., measurements generated by a blood glucose meter or a continuous glucose monitor).

The meal data 224, meanwhile, is related to meals that have been consumed by the subject. The meal data 224 may be reported by the subject. For example, the meal data 224 may include image(s) of meals that have been captured by the subject. Additionally or alternatively, the meal data 224 may include information that has been provided by the subject regarding meals, such as the foodstuff(s) included in the meal, the name of a restaurant, the location of the meal, the time of the meal, etc. In some embodiments, at least some of the meal data 224 is automatically derived on behalf of the subject (e.g., without requiring any input from the subject). For example, the diabetes management platform 200 may establish the time of a meal by examining metadata associated with an image of the meal that has been uploaded by the individual.

As shown in FIG. 1, an individual can interface with the diabetes management platform 200 via an interface. The individual may be a person with diabetes or another person with an interest in the blood glucose level of the person with diabetes.

The diabetes management platform 200 can include one or more processors 202, a communication module 204, a graphical user interface (GUI) module 206, a processing module 208, an excursion detection module 210, a classification module 212, a model module 214, a meal detection module 216, an analytics module 218, and one or more storage modules 220. In some embodiments a single storage module includes multiple computer programs for performing different operations (e.g., format conversion and statistical analysis), while in other embodiments each computer program is hosted within a separate storage module. Embodiments of the diabetes management platform 200 may include some or all of these components, as well as other components not shown here.

The processor(s) 202 can execute modules from instructions stored in the storage module(s) 220, which can be any device or mechanism capable of storing information. For example, the processor(s) 202 may execute the GUI module 206, processing module 208, excursion detection module 210, classification module 212, model module 214, meal detection module 216, or analytics module 218.

The communication module 204 can manage communications between various components of the diabetes management platform 200. The communication module 204 can also manage communications between the computing device on which the diabetes management platform 200 resides and another computing device.

For example, the diabetes management platform 200 may reside on a mobile phone in the form of a mobile application. In such embodiments, the communication module 204 can facilitate communication with a network-accessible computer server responsible for supporting the mobile application. The communication module 204 may facilitate communication with various data sources through the use of application programming interfaces (APIs), bulk data interfaces, etc.

As another example, the diabetes management platform 200 may reside on a server system that includes one or more network-accessible computer servers. In such embodiments, the communication module 204 can communicate with a computer program executing on the computing device associated with the individual. Those skilled in the art will recognize that the components of the diabetes management platform 200 can be distributed between the server system and the computing device associated with the individual in various manners. For example, some data (e.g., the physiological data 222 and the meal data 224) may reside on the computing device of the individual, while other data (e.g., the processing operations for detecting excursions in the physiological data 222 and rule sets for identifying recommendations, generating reports, etc.) may reside on the server system. The individual may be able to specify (e.g., via a privacy setting accessible on the computing device) which data, if any, is transmitted to the server system, made accessible to the server system, etc. For example, the individual may be permitted to specify that the diabetes management platform 200 can only examine images of meals that the individual has chosen to upload to the server system.

The GUI module 206 can generate the interface(s) through which an individual can interact with the diabetes management platform 200. For example, an interface may include a graphical representation of the blood glucose level over time. The graphical representation may be based on explicit data values, imputed data values, or any combination thereof. In some embodiments, images of meals (or links to such images) may be collocated alongside the graphical representation of the blood glucose level. Thus, the individual may be able to readily discover which meal caused a given excursion in the blood glucose level by interacting with (e.g., by clicking on or hovering over) the data value(s) that define the excursion. As another example, an interface may present recommendations for improving the glycemic health state (e.g., by refraining from consuming meals that negatively impacted the glycemic health state in the past).

The processing module 208 can apply one or more operations to the physiological data 222 by the diabetes management platform 200. Physiological data 222 specifying the blood glucose level of an individual could be generated by a glucose monitoring device. Examples of glucose monitoring devices include continuous glucose monitors and blood glucose meters. A glucose monitoring device may be configured to continuously or periodically transmit physiological data 222 to the diabetes management platform 200. In some embodiments, the glucose monitoring device continually uploads physiological data 222 to the diabetes management platform 200 so long as the glucose monitoring device remains communicatively coupled to the computing device on which the diabetes management platform 200 resides (e.g., via a Bluetooth® communication channel). In other embodiments, the glucose monitoring device uploads physiological data 222 to the diabetes management platform 200 on a periodic basis (e.g., hourly, daily, or weekly). In such embodiments, the physiological data 222 may include multiple datasets (e.g., a first dataset for a first time interval, a second dataset for a second time interval, etc.). Each time interval could be associated with, and correspond to, a natural rhythm or cycle. Examples of natural rhythms/cycles include a circadian cycle, a menstrual cycle, a feeding cycle, an elimination cycle, etc.

The processing module 208 can process the physiological data 222 into a format suitable for the other modules (e.g., the excursion detection module 210, classification module 212, model module 214, analytics module 216, sensor management module 218, or storage module(s) 220). The processing module 208 can also parse the physiological data 222 to identify certain characteristic(s) of the blood glucose level. For example, the processing module 208 may calculate metrics that are critical in guiding diabetes treatment in a personalized manner. These metrics can include time-in-range, glycemic variability, glycemic exposure, hypoglycemia range, hyperglycemia range, etc.

The processing module 208 can also apply one or more operations to the meal data 224 acquired by the diabetes management platform 200. Meal data 224 related to meals that have been consumed by an individual could be generated by a computing device associated with the individual. For example, before consuming a meal, the individual may use a mobile phone to capture an image of the meal. In some embodiments the individual may be prompted to upload the image to the diabetes management platform 200, while in other embodiments the image may be automatically uploaded to the diabetes management platform 200 (e.g., in accordance with a privacy setting specified by the individual). The processing module 208 can process the meal data 224 into a format suitable for the other modules (e.g., the meal detection module 216, analytics module 218, or storage module(s) 220). For example, before storing an image in a storage module 220, the processing module 208 may compress the image.

The excursion detection module 210 can examine the physiological data 222 to detect excursions in the blood glucose level. Each excursion is defined by one or more data values specifying the blood glucose level at corresponding time(s). More specifically, the excursion detection model 210 can parse the physiological data 222 to detect a signal feature that should be flagged for further analysis. Examples of signal features include:

- a minimum blood glucose value;
- a maximum blood glucose value (also referred to as a "peak blood glucose value");
- a total area beneath the peak blood glucose value (i.e., an integral of a glucose trace over the duration of the peak blood glucose value);
- an area beneath the glucose trace during the duration that is outside the glycemic range recommended by the American Diabetes Association (ADA);
- a recovery rate following the peak blood glucose value;
- a recovery rate following the minimum blood glucose value (e.g., due to consumption of a foodstuff); and
- a time characteristic of the peak blood glucose value or the minimum blood glucose value.

The recovery rates may be used to determine how symmetric the minimum or peak blood glucose values are. The time characteristic, meanwhile, could be the actual time (e.g., 8:00 AM, 10:30 AM, etc.), the day of the week, or an indication of the time interval. For example, the excursion detection model 210 may simply specify whether a glycemic event, such as a meal, occurred during the morning interval, afternoon interval, evening interval, or night interval.

Thus, while some excursions may be defined by blood glucose level variations exceeding a specified amount, other excursions may be based on the magnitude of a single data value (e.g., in the case of the minimum and peak blood glucose values). Similarly, the excursion detection module 210 may identify excursions by applying processing algorithm(s) to identify data value(s) that match a pattern in accordance with a pattern-defining parameter. Additionally or alternatively, the excursion detection module 210 could train a classification model to identify the data value(s) responsive to a determination that a matching window of physiological data corresponds to a meal. A "matching window" is a segment of physiological data 222 that temporally matches the glycemic event. The classification model may be trained using a supervised machine learning algorithm.

The classification module 212 can classify each excursion as being indicative of a glycemic event. For example, the classification module 212 may discover, based on the arrangement of data value(s), that a given excursion is indicative of a physiological response to a meal. Because each glycemic event is digitally represented by the data value(s) defining the excursion, a glycemic event can be thought of as a logical categorization of the signal feature and/or the data value(s).

The model module 214 can design a personalized statistical model based on the explicit data values included in the physiological data 222. Using the statistical model, the model module 214 can impute data values representative of estimated blood glucose measurements. The model module 214 can examine explicit data values to identify a feature indicative of a glycemic characteristic of the subject, and then design the statistical model based on the explicit data values, the feature, the glycemic characteristic, or any combination thereof. In some embodiments, each explicit data value corresponds to a time at which the explicit data value was generated. In such embodiments, the model module 214 may also consider these times (also referred to as "time points") when designing the statistical model. Several different models can be designed by the model module 214.

For example, the model module 214 may be configured to construct a Gaussian process model. In such embodiments, the model module 214 can use a radial basis function kernel designed to capture a correlation timescale and a periodic kernel designed to capture typical periodic patterns (e.g., daily, weekly, or monthly patterns). The radial basis function kernel is typically designed to indicate that the blood glucose level is less likely to change over short time intervals (e.g., several seconds) than long time intervals (e.g., several hours). The periodic kernel, meanwhile, can be designed to ensure that imputed data values conform with a periodic pattern of past explicit data values associated with the subject.

As another example, the model module 214 may be configured to construct a Kalman filtering model (also referred to as "linear quadratic estimation model"). In such embodiments, the model module 214 can track variance values indicative of the uncertainty of the imputed data values. By estimating a joint probability distribution over the imputed data values, the model module 214 can increase imputation accuracy over other techniques that are based on a single measurement. The model module 214 can also update the imputed data values and/or the variance values using a state transition model. The state transition model can be based on ordinary differential equation(s) representing the relevant biological responses. In some embodiments the ordinary differential equation(s) are adaptively personalized based on characteristic(s) of the subject, while in other embodiments the ordinary differential equation(s) are statically programmed based on biological literature.

An example of a potential form for an ordinary differential equation is provided by Makroglou et al. in "Mathematical models and software tools for the glucose-insulin regulatory system and diabetes: an overview," *Applied Numerical Mathematics*, 56(3-4):559-573, 2006; Chervoneva et al. in "Estimation of nonlinear differential equation model for glucose-insulin dynamics in type 1 diabetic patients using generalized smoothing," *The Annals of Applied Statistics*, 8(2):886-904, 2014; and De Gaetano et al. in "Mathematical modeling of the intravenous glucose tolerance test," *Journal of Mathematical Biology*, 40(2):136-168, 2000.

$$\frac{dG}{dt} = -b_1 G - b_4 IG + b_7 + S_G(t) \quad \text{(Eq. 1)}$$

$$\frac{dI}{dt} = -b_2 I + \frac{b_6}{b_5} \int_{-\infty}^{\tau} G(s) e^{\frac{s-t}{b_5}} ds + S_I(t) \quad \text{(Eq. 2)}$$

where
G Blood glucose level;
I Blood insulin level;
$S_G$ Rate at which glucose enter the blood due to food consumption;
$S_I$ Insulin injection term; and
$b_j$ Various parameters from relevant literature (e.g., $b_4$ may measure insulin sensitivity).
Given the following constraints:
1. All parameters and variables >0.
2. $\min(S_{G,I})=0$.
3. A factor enforcing that $S_{G,I}$ be considered "sparse."
With the definition of an auxiliary variable (X) as $$X = \frac{b_6}{b_5} \int_{-\infty}^{\tau} G(s) e^{(s-t)/b_5} ds, \quad \text{(Eq. 3)}$$

the integro-differential equation specifies in equations 1-2 can be transformed into a simple third-order ordinary differential equation.

$$\frac{dX}{dt} = \frac{b_6}{b_5} G - \frac{1}{b_5} X \quad \text{(Eq. 4)}$$

$$\frac{dI}{dt} = -b_2 I + X + S. \quad \text{(Eq. 5)}$$

The equilibrium solution to equations 4-5 is:

$$\tilde{G} = \frac{-b_1 + \sqrt{b_1^2 + 4b_4 b_6 b_7 / b_2}}{2 b_4 b_6 / b_2} \quad \text{(Eq. 6)}$$

$$\tilde{I} = b_6 \tilde{G}/b_2 \quad \text{(Eq. 7)}$$

$$\tilde{X} = b_6 \tilde{G}. \quad \text{(Eq. 8)}$$

As noted above, the model module 214 can apply the statistical model to the explicit data values to impute one or more data values. These imputed data values represent estimates of the physiological state of the subject. For example, if the physiological data 222 includes explicit data values specifying the blood glucose level of the subject over a first time interval, then the model module 214 can impute data values for the blood glucose level of the subject over a second time interval.

The meal detection module 216 can examine the meal data 224 to identify meals that have been consumed by the subject. Moreover, the meal detection module 216 may segment the meal data 224 by meal. Thus, the meal data 224 may include multiple datasets, each of which corresponds to a different meal consumed by the subject.

The meal data 224 can include images of meals that have been captured by the subject. In such embodiments, the meal detection module 216 may apply one or more processes to the images. These processes can include image processing, feature analysis, and data classification. By applying these process(es), the meal detection module 216 may be able to determine which foodstuffs, if any, are included in each image. By applying these process(es), the meal detection module 216 may also be able to infer information regarding a meal, such as the meal type (e.g., whether the meal corresponds to breakfast, lunch, dinner, or a snack). For example, the meal detection module 216 may infer that an image corresponds to breakfast upon determining that the image is likely to include eggs or cereal.

Additionally or alternatively, the meal data 224 can include information regarding the meals that have been consumed by the subject. The information may specify the foodstuff(s) included in a meal, the name of a restaurant, the location of the meal, the time of the meal, the meal type, etc. The information can be acquired in several different ways. In some instances, the subject manually inputs the information regarding a meal before, during, or after the meal. For example, before consuming a meal, the subject may initiate a mobile application executing on his/her mobile phone, and then input information regarding the meal into an interface generated by the mobile application. In other instances, the meal detection module 216 automatically derives the information without requiring any input from the individual. For example, the meal detection module 216 may establish the time of a meal by extracting a timestamp from metadata associated with an image of the meal. As another example, the meal detection module 216 may examine unstructured data (e.g., journal entries created by the subject) to generate structured data related to a meal. For instance, upon reviewing a text-heavy journal entry created by the subject, the meal detection module 216 may discover words/phrases that indicate which foodstuff(s) were consumed, which individual(s) were present, the meal type, etc.

As noted above, the classification module 212 can classify excursions in the physiological data 222 as being indicative of glycemic events. For each excursion that has been classified as being indicative of a physiological response to a meal, the analytics module 218 may apply a matching algorithm to identify a matching meal in the meal data 224. Alternatively, the analytics module 218 may apply a matching algorithm to identify a matching excursion for each meal discovered in the meal data 224. The excursion corresponding to a given meal will usually follow the given meal within a specified interval of time. This interval of time may differ from subject to subject. Thus, the matching algorithm may be personalized for each subject (e.g., to account for a glycemic characteristic of the subject, or based on past glycemic response delays).

Moreover, the analytics module 218 can perform one or more analytic processes based on the physiological data 222, meal data 224, or any combination thereof. In some embodiments, the analytics module 218 performs an analytic process using a specific window of physiological data 222 corresponding to a meal. Such action may be performed selectively. For instance, the analytics module 218 may only perform the analytic process(es) responsive to discovering the meal has been classified as a negative glycemic event likely to negatively affect the glycemic health of the subject, a positive glycemic event likely to positively affect the glycemic health of the subject, or a neutral glycemic event that is unlikely to affect the glycemic health of the subject. Examples of analytic processes include generating post-glycemic event reports, prioritizing recommendations for improving the glycemic health state of the subject, examining glucose-related metrics critical in guiding diabetes treatment in a personalized manner, etc. In some embodiments, the analytics module 218 is programmed to produce a recommendation for improving the glycemic health state of the subject if a meal has been classified as a negative glycemic event. The recommendation may request, for example, that the subject refrain from consuming the meal.

Imputing Data Values

Glucose traces enable individuals to readily observe how consumption of a meal has affected the blood glucose level. Generally, the blood glucose level will rapidly increase following the ingestion of a foodstuff and then steadily decrease thereafter. Foodstuffs having a high glycemic index will be more rapidly digested, and thus cause substantial fluctuations in the blood glucose level over a short period of time.

Figure 3:
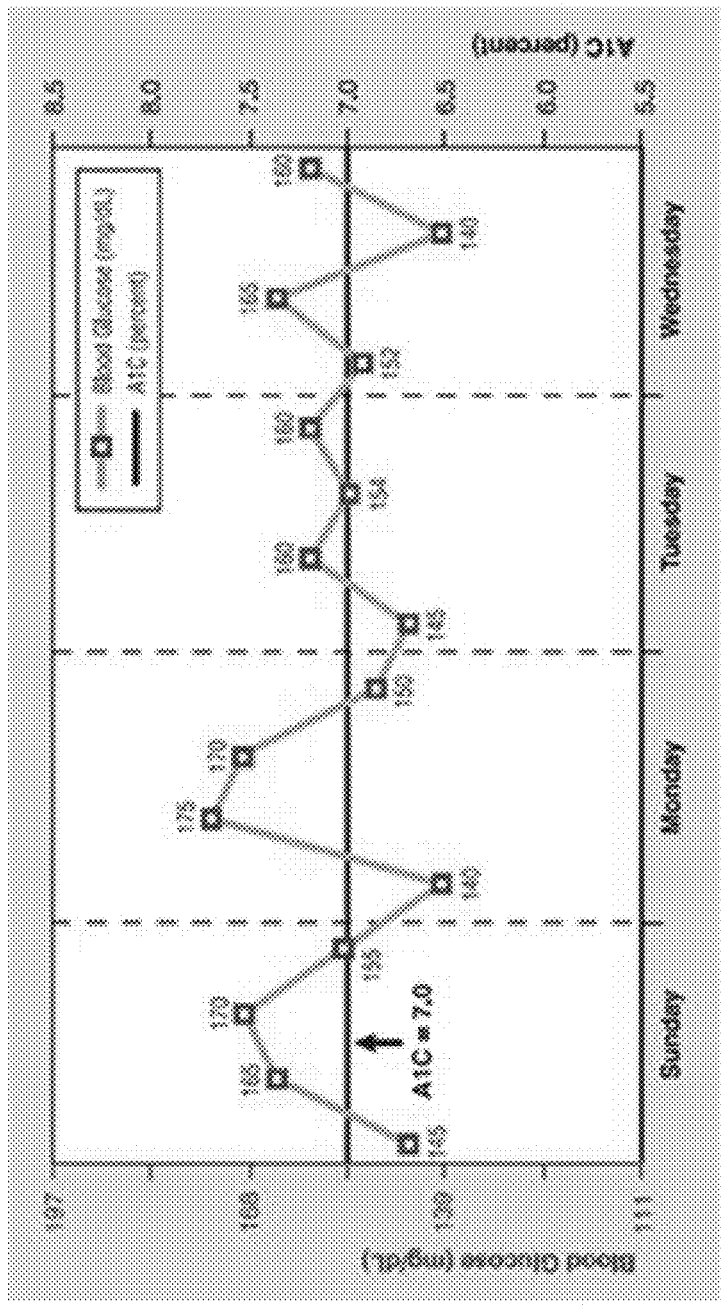
FIG. 3 depicts an example of a glucose trace that has been constructed from a series of measurements generated by a blood glucose meter during sequential administrations of an A1c test over the course of several days.

Historically, individuals with diabetes have monitored their blood glucose level by examining measurements generated by a blood glucose meter. FIG. 3 depicts an example of a glucose trace that has been constructed from a series of measurements generated by a blood glucose meter during sequential administrations of an A1c test over the course of several days. However, because the glucose trace shown in FIG. 3 is based on static glucose measurements generated by a blood glucose meter, the glucose trace can be misleading. For example, past glucose measurements are not necessarily indicative of future glucose measurements. Therefore, direct comparisons of time intervals (e.g., consecutive days) are often inaccurate or improper. Moreover, sporadic glucose measurements can make it difficult to draw meaningful conclusions for a time interval. For example, variations in the blood glucose level can easily be overestimated, underestimated, or missed entirely if an individual only performs the A1c test three or four times per day.

Figure 4:
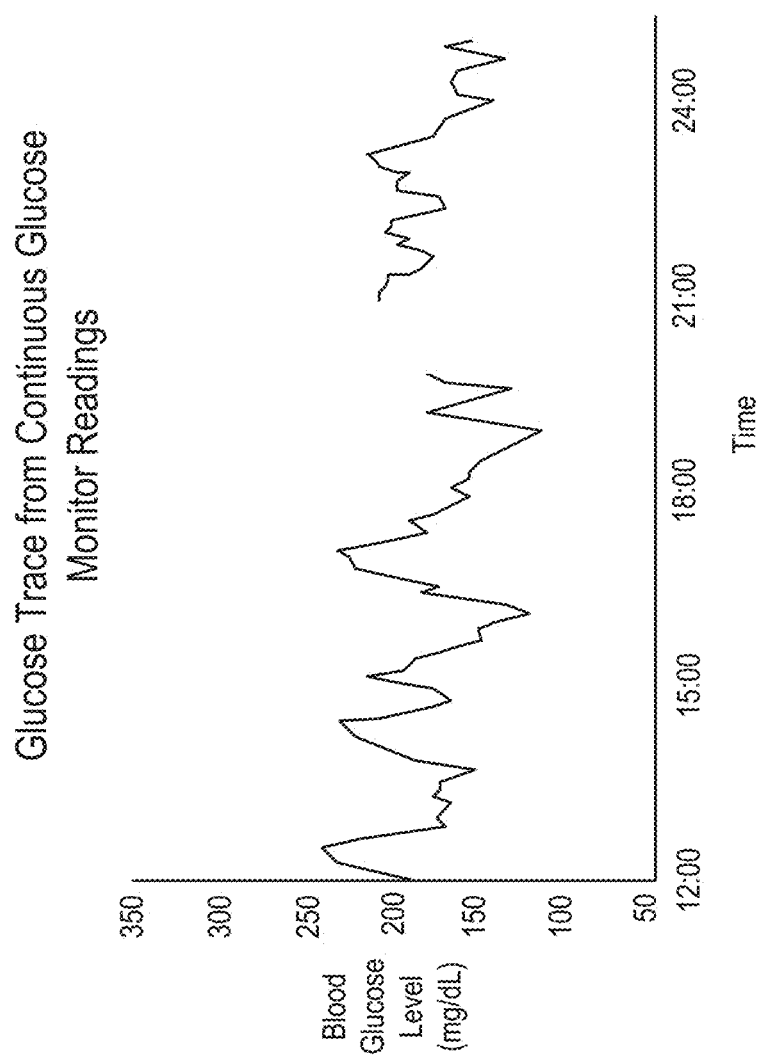
FIG. 4 depicts an example of a glucose trace that has been constructed from a series of measurements generated by a continuous glucose monitor over the course of a 12-hour period.

To address these shortcomings, some individuals have begun using continuous glucose monitors to continually monitor blood glucose level throughout the day. FIG. 4 depicts an example of a glucose trace that has been constructed from a series of measurements generated by a continuous glucose monitor over the course of a 12-hour period. However, these glucose traces can be difficult to qualitatively interpret, even for professional diabetes educators and health coaches responsible for monitoring the glycemic health of individuals with diabetes (also referred to as "subjects" or "patients").

Introduced here are computer programs and associated computer-implemented techniques for imputing glucose measurements based on explicit glucose measurements generated by a glucose monitoring device, such as a blood glucose meter or a continuous glucose monitor. As further described below, a diabetes management platform (e.g., the diabetes management platform 200 of FIG. 2) can enable an intelligent design of a personalized statistical model (also referred to as an "imputation model") for imputing data values for the blood glucose level of a subject.

Figure 5:
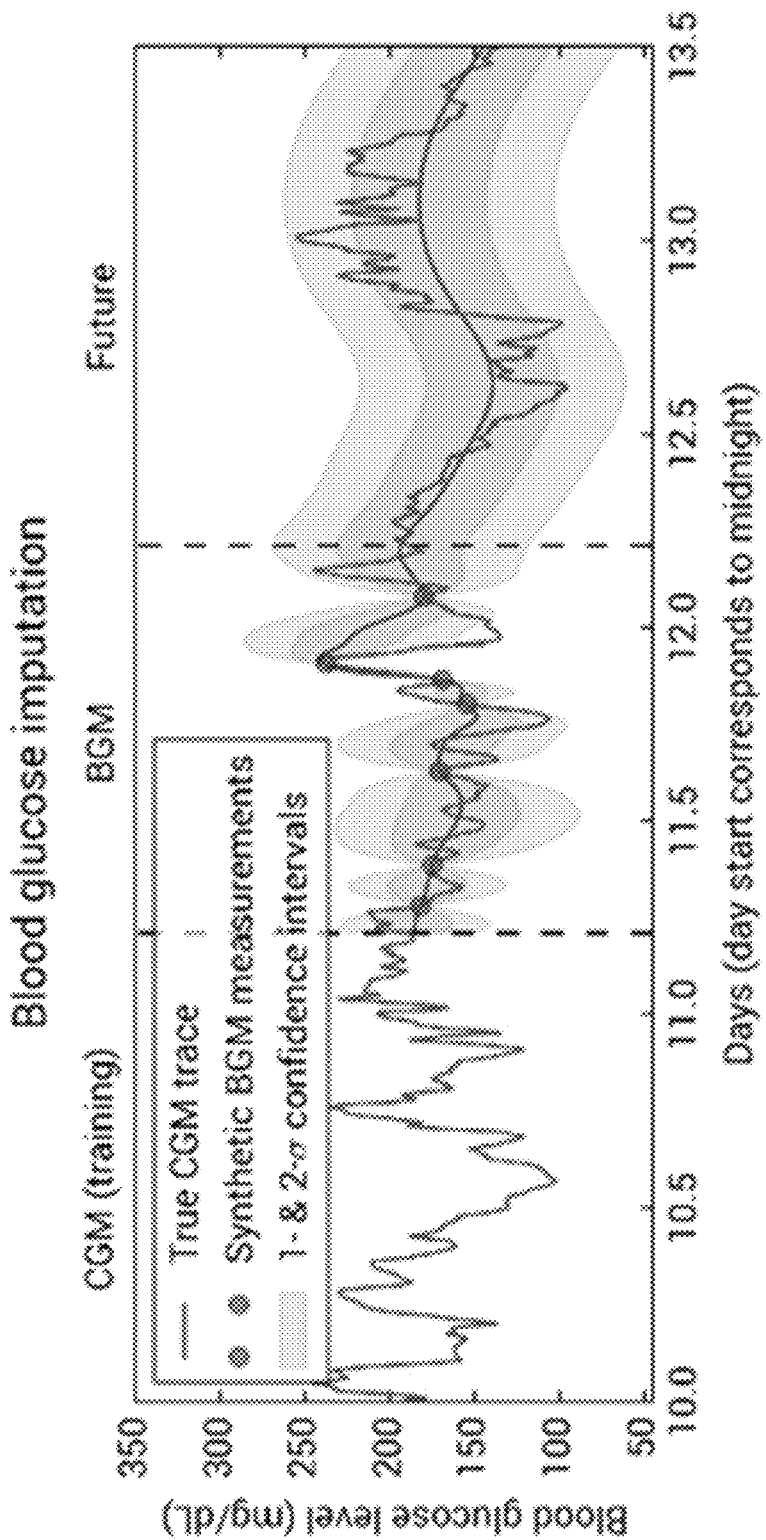
FIG. 5 illustrates how the diabetes management platform can design a statistical model for imputing future glucose measurements based on a first set of explicit glucose measurements included in training data.

FIG. 5 illustrates how the diabetes management platform can design a statistical model for imputing future glucose measurements based on a first set of explicit glucose measurements included in training data. An imputation model has been trained to fit 11 days of physiological data to the left of the first dashed vertical line. Here, the imputation model has also been fed 7 synthetic data values in the spirit of ad hoc measurements generated by a blood glucose meter. The gray confidence intervals illustrate where the imputation model believes subsequent data values are likely to reside.

In between the synthetic data values, the imputation model can interpolate the blood glucose level. Consequently, the uncertainty (e.g., represented as the width of the confidence intervals) may increase as the distance from the nearest synthetic data value increases. Outside of the region where these synthetic measurements exist, the imputation model can retreat to previously observed patterns (e.g., daily or weekly patterns).

In general, the diabetes management platform will initially examine explicit glucose measurements during a training period. The glucose monitoring device may be a continuous glucose monitor or a blood glucose meter. Here, for example, the first set of explicit glucose measurements is generated by a continuous glucose monitor. However, those skilled in the art will recognize that the first set of explicit glucose measurements could additionally or alternatively include values generated by a blood glucose meter.

The diabetes management platform may also consider a second set of explicit glucose measurements included in training data. Here, for example, the second set of explicit glucose measurements is generated by a blood glucose meter (BGM) on an ad hoc basis. These explicit glucose measurements are labeled as synthetic BGM measurements in FIG. 5. The diabetes management platform may use the second set of explicit glucose measurements to refine the statistical model, improve the accuracy of imputed glucose measurements, etc. In some instances, the diabetes management platform only examines a single set of explicit glucose measurements (e.g., either the first set of explicit glucose measurements or the second set of explicit glucose measurements) when designing the statistical model.

Each set of explicit glucose measurements may be associated with a different time interval. For example, the first set of explicit glucose measurements may correspond to a first time interval and the second set of explicit glucose measurements may correspond to a second time interval. These time intervals may be directly adjacent to one another as shown in FIG. 5.

The diabetes management platform can use the explicit glucose measurements to impute glucose measurements for a future time interval. For example, the diabetes management platform may examine imputed glucose measurements associated with a past time interval to impute glucose measurements for a future time interval. As another example, the diabetes management platform may examine explicit glucose measurements generated by a blood glucose meter, and then create a visualization of imputed glucose measurement(s) for review by an individual. The individual may be the subject whose blood glucose level is being monitored or a health coach responsible for monitoring the blood glucose level of the subject.

In some embodiments, the visualization specifies the predicted blood glucose level at a specific time (e.g., "The blood glucose level is expected to be approximately 180 mg/dl at 12 PM."). In other embodiments, the visualization is a glucose trace that is indicative of an approximation of continuous monitoring of the blood glucose level. Thus, the glucose trace based on the imputed glucose measurement(s) may predictively mimic continuous monitoring by a continuous glucose monitor. The visualization may also include a bar plot showing the estimated blood glucose level of a time interval during which the subject hasn't yet taken an explicit glucose measurement. The bar plot may include one or more error bars overlaying the glucose trace. These error bar(s), which can correspond to different confidence interval(s), visually illustrate where the diabetes management platform expects imputed data values to reside. FIG. 5, for example, includes a first error bar corresponding to a confidence interval of one standard deviation and a second error bar corresponding to a confidence interval of two standard deviations.

Generally, training of the statistical model occurs before execution of the imputation process. Training can be done in several different ways.

For example, the diabetes management platform may examine a dataset for an individual corresponding to a past time interval. In such embodiments, the diabetes management platform could train the statistical model on the dataset and then impute values for an upcoming time interval.

As another example, the diabetes management platform may examine a dataset for an individual that includes a first subset (e.g., for a morning time interval) and a second subset (e.g., for an evening time interval). In such embodiments, the diabetes management platform could train the statistical model on the first subset and then impute additional values for the first subset. Additionally or alternatively, the diabetes management platform could train the statistical model on the first subset and then impute additional values for the second subset.

As another example, the diabetes management platform may examine a first dataset for a first individual and a second dataset for a second individual. These individuals may share a characteristic in common, such as age, ethnicity, activity level, diabetes classification, etc. In such embodiments, the diabetes management platform could train the statistical model on the first dataset and then impute additional values for the second dataset. Because blood glucose level is often highly dependent on the characteristics/circumstances of the corresponding individual, this type of training process may be avoided in favor of more personalized training processes.

Figure 6:
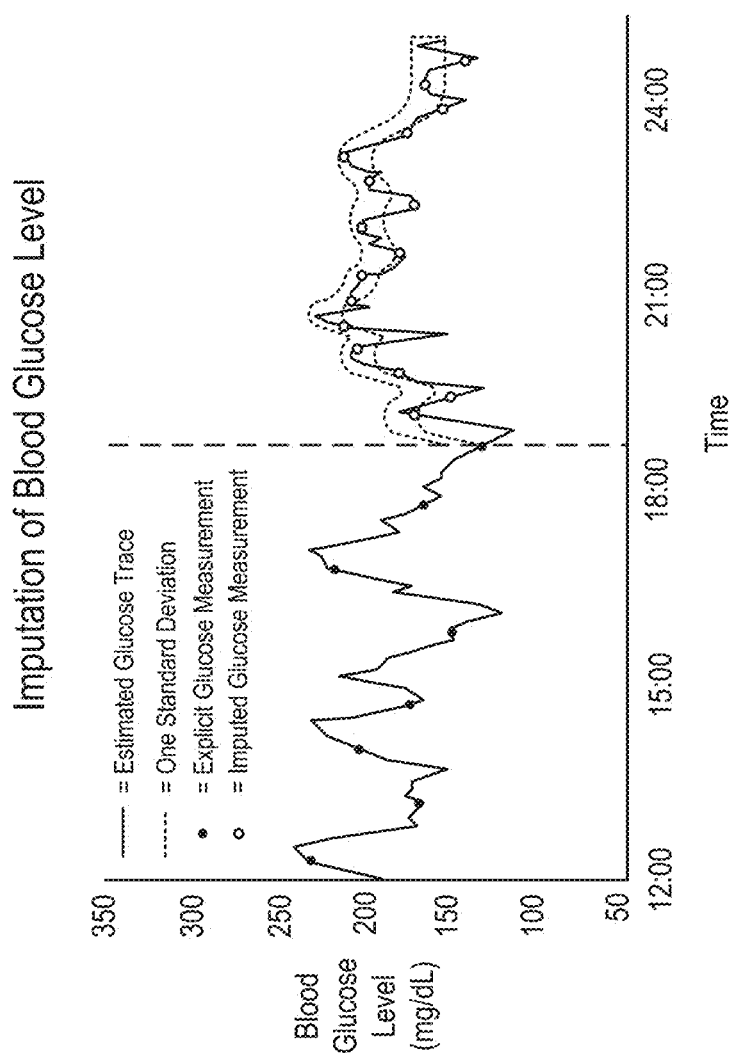
FIG. 6 illustrates how the diabetes management platform may dynamically modify the bar plot as additional explicit glucose measurements are acquired over time.

FIG. 6 illustrates how the diabetes management platform may dynamically modify the bar plot as additional explicit glucose measurements are acquired over time. The diabetes management platform can, upon acquiring a new explicit glucose measurement, modify the bar plot to reflect the increase in certainty of the blood glucose level of the subject. For example, the diabetes management platform may monitor the duration since the most recent explicit glucose measurement. As the duration increases, the diabetes management platform may modify the bar plot by dynamically altering the width of the error bar(s). Increases in the width may be substantially proportional to increases in the duration.

Upon acquiring the new explicit glucose measurement, the diabetes management platform may replace a corresponding imputed glucose measurement with the new explicit glucose measurement. Generally, the corresponding imputed glucose measurement will be the closest past imputed glucose measurement. For example, if the diabetes management platform generates an imputed glucose measurement every half hour on the hour (e.g., 12:00, 12:30, 13:00, etc.), then an explicit glucose measurement taken at 12:55 will correspond to the imputed glucose measurement at 12:30. An explicit glucose measurement may correspond to multiple imputed glucose measurements if the time since the last explicit glucose measurements exceeds the periodicity of the imputed glucose measurements.

In some embodiments, imputed glucose measurements are visually distinguishable from explicit glucose measurements. In other embodiments, only imputed glucose measurements or explicit glucose measurements may be visible. For example, a visualization may include a visual representation of each explicit glucose measurement and an estimated glucose trace indicative of the imputed glucose measurements.

The diabetes management platform may also dynamically collapse the error bar(s) to indicate an increase in certainty of the blood glucose level due to the acquisition of the new explicit glucose measurement. Such action can incentivize subjects to administer the A1c test more frequently, thereby providing health coaches with more data to use when coaching the subjects. These techniques can be used in addition to, or instead of, conventional incentive techniques (e.g., affirmative messages and graphical illustrations of balloons/confetti/etc.).

Those skilled in the art will recognize that some individuals may prefer to see a mix of explicit and imputed glucose measurements (as shown in FIG. 6), while other individuals may prefer to see only imputed glucose measurements for upcoming time intervals (not shown).

Figure 7:
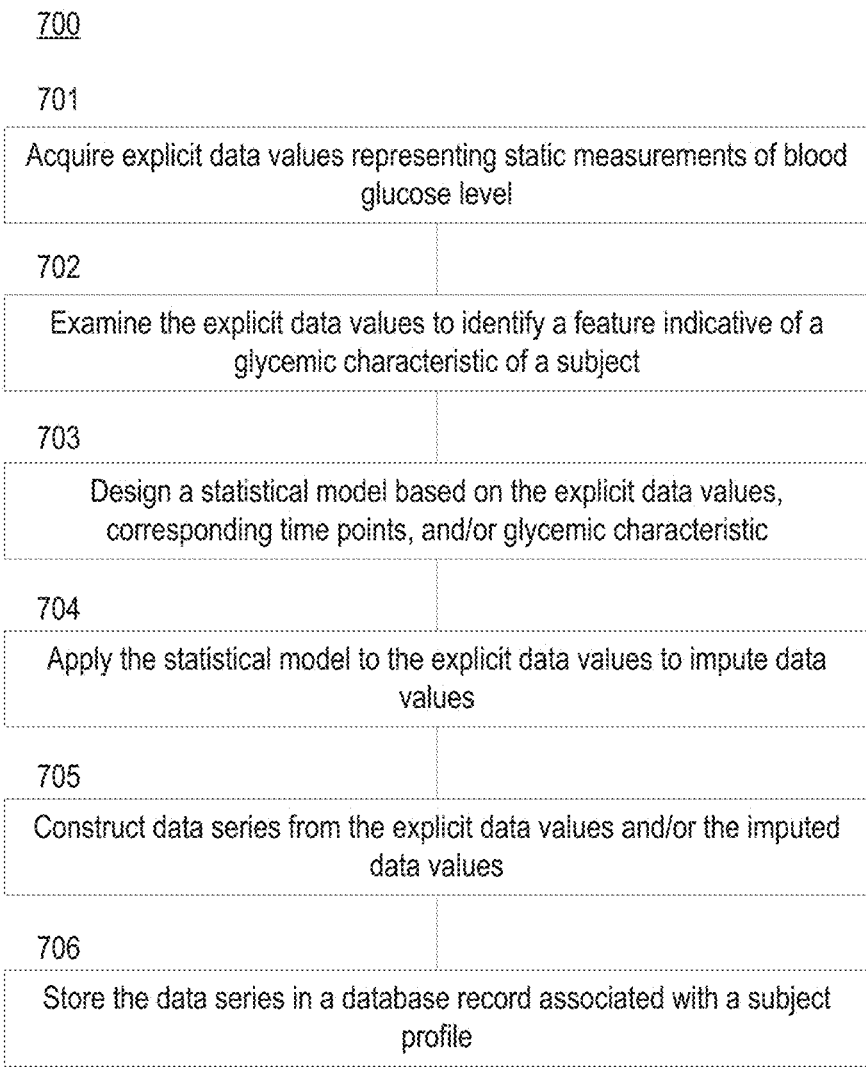
FIG. 7 depicts a flow diagram of a process for producing a statistical model for probabilistically imputing data values where explicit data values have not been generated.

FIG. 7 depicts a flow diagram of a process 700 for producing a statistical model for probabilistically imputing data values where explicit data values have not been generated. These imputed data values may be used to guide an individual toward a healthier glycemic state. For example, a diabetes management platform may examine the imputed data values to discover whether they are indicative of healthy or unhealthy blood glucose measurements. Such action may permit the diabetes management platform to recommend certain actions be performed or refrained from during an upcoming time interval.

Initially, the diabetes management platform acquires multiple explicit data values representing static measurements of the blood glucose level of a subject (step 701). Each explicit data value may correspond to a different time point. Thus, the diabetes management platform may construct a data series from the explicit data values that includes discrete, digitally represented values in a temporal order that are indicative of time-varying glucose concentration sampled on an ad hoc basis.

The diabetes management platform can then examine the explicit data values to identify a feature indicative of a glycemic characteristic of the subject (step 702). The glycemic characteristic may be, for example, diabetes classification, blood glucose level trend(s) over certain time period(s), periodicity of the explicit data values, maximum data value, minimum data value, etc. The diabetes management platform can design a statistical model based on the explicit data values, the corresponding time points, the glycemic characteristic, or any combination thereof (step 703).

For example, the statistical model may be a Gaussian process model. In such embodiments, the diabetes management platform can create a radial basis kernel that indicates the blood glucose level is more likely to vary over long time intervals (e.g., hours) than short time intervals (e.g., seconds) and a periodic kernel that ensures any imputed data values conform with a periodic pattern of past explicit data values. The periodic pattern may be based on a series of past explicit data values taken over the course of a day, week, month, etc.

As another example, the statistical model may be a Kalman filtering model. In such embodiments, the diabetes management platform can, for each imputed data value, produce an estimated value indicative of the predicted blood glucose level at a future time, generate a variance measure indicative of the uncertainty of the estimated value, and periodically update the estimated value or the variance measure using a state transition model. The state transition model can be based on ordinary differential equation(s) representing the relevant biological responses. In some embodiments the ordinary differential equation(s) are adaptively personalized based on biological characteristic(s) of the subject, while in other embodiments the ordinary differential equation(s) are statically programmed based on biological literature.

The diabetes management platform can then apply the statistical model to the explicit data values to impute one or more data values for a future time interval where explicit data values have not been generated (step 704). Such action may require the diabetes management platform perform interpolation and/or extrapolation. Thus, for each imputed data value, the diabetes management platform can either interpolate the imputed data value from at least one explicit data value located within a certain proximity or extrapolate the imputed data value from a periodic pattern responsive to a determination that no explicit data values exist within the certain proximity. The certain proximity may be automatically determined by the diabetes management platform and/or manually specified by an individual. The certain proximity could be 30 minutes, 1 hour, 2 hours, 4 hours, etc.

Thus, the diabetes management platform may interpolate the blood glucose level between explicit data values taken on an ad hoc basis and extrapolate blood glucose level where no explicit data values exist. For example, if a Gaussian process is used for imputation, then the diabetes management platform can use as a kernel the sum of a Matérn kernel and a periodic kernel. The periodic kernel may have a fixed period of 24 hours to capture/learn daily patterns of the subject. In some instances, a statistical model may revert to previously observed daily patterns due to enforcement of a 1-day-periodicity Gaussian process kernel. A series of imputed data values can include both interpolated data values and extrapolated data values.

In some embodiments, the diabetes management platform constructs a data series that includes the explicit data values and/or the imputed data values (step 705). The data series may be indicative of an approximation of continuous monitoring of the time-varying blood glucose level of the subject. The diabetes management platform may also store the explicit and imputed data values in separate data series. Thus, the explicit data values may be stored in a first data series and the imputed data values may be stored in a second data series. The diabetes management platform can store the data series in a database record associated with a subject profile (step 706). Additionally or alternatively, the diabetes management platform may store certain explicit/imputed data values in the subject profile. For example, the diabetes management platform may track the maximum value and/or the minimum value within a certain timeframe (e.g., a day, week, or month) or across the subject's entire history with the diabetes management platform. As another example, the diabetes management platform may track mean glucose, which could be updated over time as additional explicit data values are acquired.

Discovering Excursions in Physiological Data

As noted above, a diabetes management platform may receive physiological data associated with an individual (also referred to as a "patient" or a "subject"). The physiological data can include explicit data values representative of discrete measurements of the blood glucose level of the subject, imputed data values representative of predicted measurements of the blood glucose level of the subject, or any combination thereof. The physiological data may include imputed data values if, for example, the diabetes management platform intends to gain a better understanding of the blood glucose level during a past time interval (e.g., in between a pair of explicit data values) or a future time interval (e.g., following a series of explicit data values).

Introduced here are computer programs and associated computer-implemented techniques for discovering excursions in the physiological data of a subject whose glycemic health state is being monitored and then characterizing the excursions. A diabetes management platform can apply rule set(s) to the physiological data to discover glycemic events, propose therapeutic behavior changes, etc. Thus, the diabetes management platform can automatically surface reminders regarding certain actions, interesting glycemic characteristics (e.g., the blood glucose level was abnormally low upon waking or abnormally high during the evening), etc. The diabetes management platform can provide these insights instead of, or in addition to, those offered by health coaches.

By classifying excursions detected in the physiological data, the diabetes management platform can facilitate the identification of a therapeutic behavior change intended to improve the glycemic health state of the subject. For example, a health coach may review the glycemic event(s) associated with a subject before generating a recommendation for improving the glycemic health state. As another example, the diabetes management platform may automatically generate a recommendation for improving the glycemic health state based on characteristics of the excursion(s), such as duration, frequency, magnitude, etc. As another example, the diabetes management platform may examine meal data associated with meals consumed by the subject to discover the relationship that exists between blood glucose and the foodstuff(s) included in the meals. Such action may enable the diabetes management platform to identify meal preferences of the subject, form personalized recommendations with respect to meals, etc.

Figure 8:
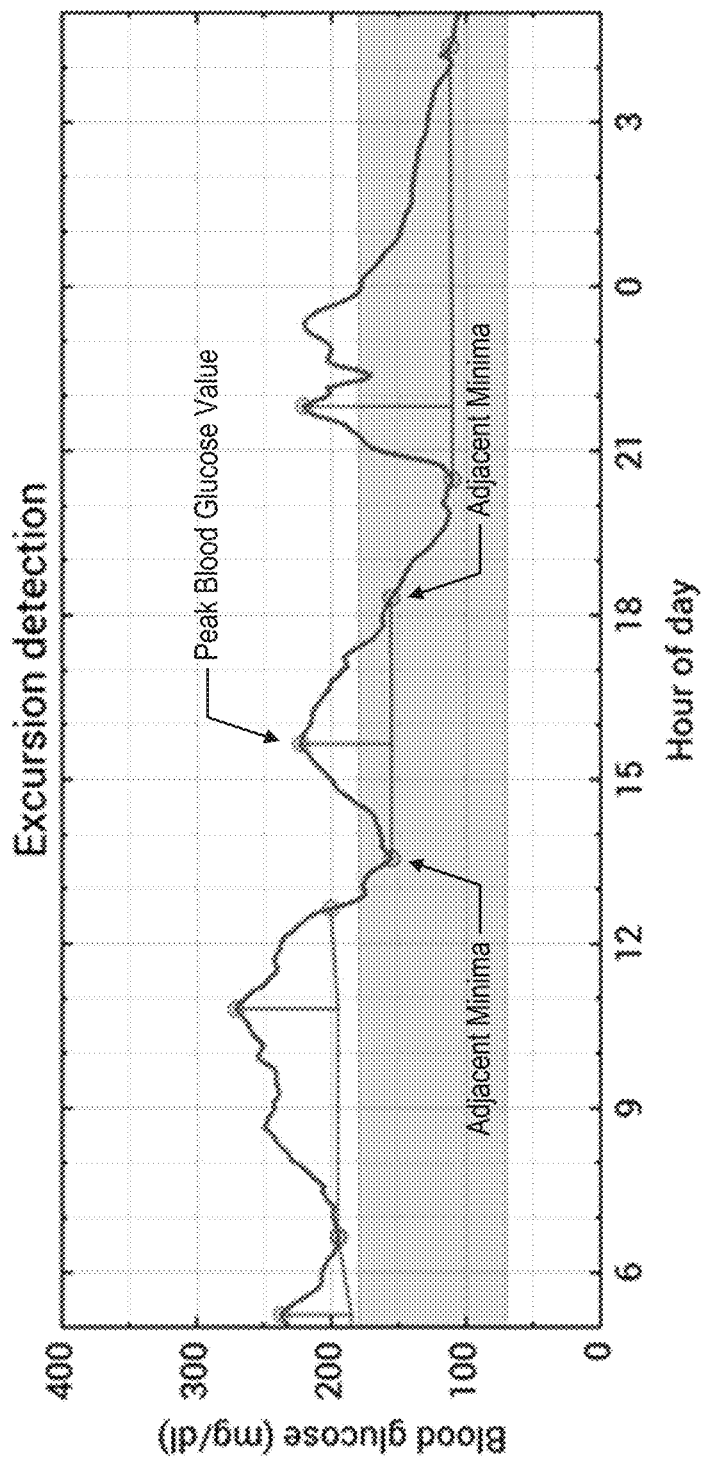
FIG. 8 illustrates how the diabetes management platform can apply processing algorithm(s) to physiological data detect excursions in the blood glucose level.

FIG. 8 illustrates how the diabetes management platform can apply processing algorithm(s) to physiological data detect excursions in the blood glucose level. As noted above, the physiological data can include explicit data values and/or imputed data values. An excursion is a variation in the blood glucose level exceeding a specified amount within a predetermined time interval. Generally, the variation will be a positive variation (e.g., due to consumption of a foodstuff), though the variation could also be a negative variation. In some embodiments excursions are detected based only on a time series of blood glucose level values, while in other embodiments excursions are detected based on other information in addition to the time series of blood glucose level values. The other information may include metadata, user input, other signals (e.g., from a glucose monitoring device, fitness tracker, mobile phone, etc.), etc. The diabetes management platform may also apply other processing algorithm(s) to detect excursions caused by other types of glycemic events. For example, some embodiments of the diabetes management platform examine the glycemic recovery following meals due to, for example, performance of an exercise activity.

By applying the processing algorithm(s), the diabetes management platform can detect semi-global minima over a configurable time interval. For example, in some embodiments, semi-global minima are discovered by employing a processing algorithm that considers two configurable parameters: timescale and height. In such embodiments, the processing algorithm can find local minima on the order of the timescale parameter (e.g., by identifying all points where the value is lower than the preceding and succeeding points), pair successive minima into excursion intervals, discard excursion intervals where the second point has a lower value than the first point, and discard excursion intervals where the peak height is less than the height parameter.

Thus, the diabetes management platform may find the time interval boundaries that permit the blood glucose level to be a global minimum within a surrounding time interval. In some embodiments the time intervals are manually defined by an individual, while in other embodiments the time intervals are automatically defined by the diabetes management platform. For example, the diabetes management platform may set the time intervals to match a natural rhythm/cycle, such as a circadian cycle, menstrual cycle, feeding cycle, elimination cycle, etc.

The diabetes management platform can then pair adjacent minima and ensure that a sufficiently large excursion occurs in between the adjacent minima. An excursion may be sufficiently large if the peak blood glucose value exceeds an upper threshold, if the difference between the peak blood glucose value and the adjacent minima exceeds a certain amount, etc. Additionally or alternatively, the excursion may be defined based on the relationship between the adjacent minima and/or the peak blood glucose value and the glycemic range recommended by the ADA. Thus, the processing algorithm(s) can include two parameters (i.e., a pair of semi-global minima and a peak value) that are fit to physiological data generated by a glucose monitoring device. While embodiments may be described in the context of semi-global minima associated with an upward excursion, the technology is similarly applicable to downward excursions. In contrast to upward excursions, downward excursions are defined by a pair of semi-global maxima and a minimal value.

Several different heuristics and/or algorithms can be implemented by the diabetes management platform to discover excursions. For example, given a time series of continuous glucose monitoring data, the diabetes management platform may detect all relative minima over windows of a certain timescale (e.g., 30 minutes, 60 minutes, 120 minutes, etc.). The diabetes management platform can pair successive minima into candidate excursion intervals, and then refine the candidate excursion intervals using one or more criteria. For example, the diabetes management platform may prevent an excursion interval from ending at a blood glucose level lower than where the excursion interval began. Moreover, the diabetes management platform may filter candidate excursion intervals having a height smaller than a certain amount (e.g., 10 mg/dl, 20 mg/dL, 30 mg/dL, etc.). These parameters (e.g., the certain timescale and the certain amount) may be personalized over time based on characteristics of the subject, such as recovery rate, average blood glucose value, etc.

In some embodiments, the diabetes management platform identifies excursions by applying patterns to detect matching parameter(s). The diabetes management platform may be communicatively coupled to a library of patterns corresponding to different glycemic events. For example, the library may include patterns that allow the diabetes management to readily identify instances of hypoglycemia, pre-sleep meals, administrations of medication, etc.

Figure 9:
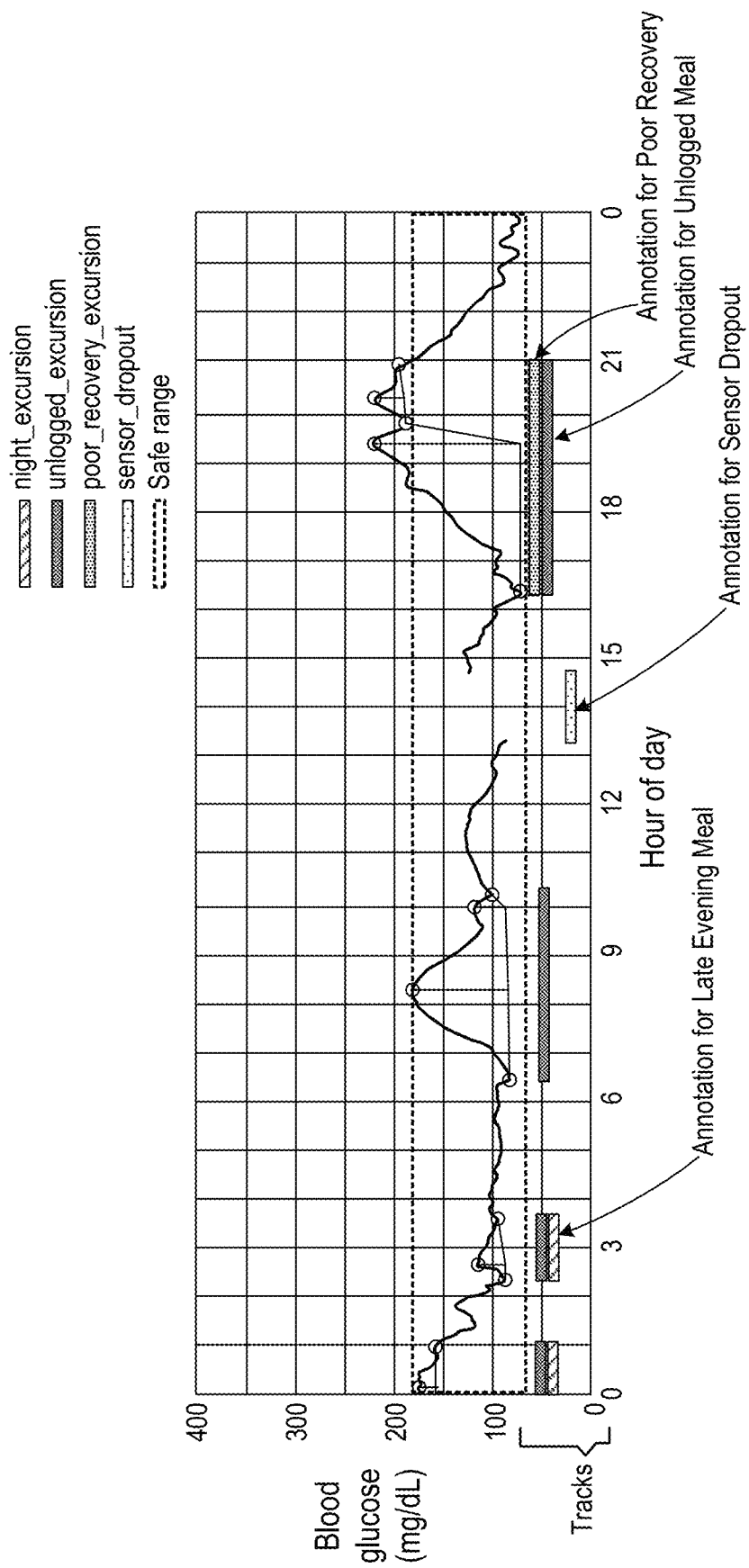
FIG. 9 illustrates how the diabetes management platform can automatically classify a variety of signal features indicative of different glycemic events.

FIG. 9 illustrates how the diabetes management platform can automatically classify a variety of signal features indicative of different glycemic events. Examples of glycemic events include:

Meals that are unrelated to any subject-logged meals catalogued in a database. Often, a subject will manually log meals through a computer program associated with the diabetes management platform. The diabetes management platform may identify excursions that don't match a corresponding logged meal (e.g., through the comparison of time metadata derived from, or included with, the physiological data to records of logged meals).

Meals that are associated with an abnormally quick glycemic recovery (e.g., a glycemic recovery exceeding an upper rate) or an abnormally slow glycemic recovery (e.g., a glycemic recovery falling below a lower rate).

Meals that will cause the blood glucose level to exceed an upper threshold following consumption of the next meal. These meals will cause the blood glucose level to enter an unsafe glycemic range following the next meal.

Meals that occur within a certain proximity of a temporal event (e.g., a sleep cycle). For example, the diabetes management platform may detect meals that are consumed by subjects late in the evening to avoid having blood glucose level drop too low during the night. Because these events can be associated with medication problems, they provide a clear intervention point.

Meals that are substantially dissimilar from other meals in a nearby time interval (e.g., occurring in the same day or week), occurring at a similar time (e.g., occurring around the same time on consecutive days), etc. In some embodiments dissimilar meals are "bad" meals surrounded by "good" meals, while in other embodiments dissimilar meals are "good" meals surrounding by "bad" meals. A "bad" meal will generally cause the blood glucose level to exceed the upper threshold of the glycemic range recommended by the ADA. A "good" meal, meanwhile, will generally cause the blood glucose level to remain within the glycemic range recommended by the ADA.

Periodic patterns in the blood glucose value. For example, the diabetes management platform may detect that a subject struggled to stay within the recommended glycemic range during certain time periods (e.g., mornings, afternoons, evenings, or nights). Moreover, the diabetes management platform can infer information about the corresponding meals (i.e., breakfast, lunch, dinner, or sporadic snacks) based on the certain time periods.

Blood glucose values exceeding an upper threshold (e.g., 180 mg/dl, 200 mg/dL, 225 mg/dL, etc.).

Blood glucose values falling below a lower threshold (e.g., 60 mg/dl, 80 mg/dL, 100 mg/dL, etc.).

Time intervals corresponding to glucose monitoring device-related issues. Examples of such issues include sensor dropout, faulty excursion data values, etc. The diabetes management platform may detect when sensor dropouts occur from gaps in physiological data. Sensor dropouts may be an indicator of poor placement/fit, replacement, etc.

Hypoglycemic events. Some glucose monitoring devices can generate hypoglycemia alerts based on a direct comparison of the blood glucose level to one or more thresholds. For example, some glucose monitoring devices generate alerts upon detecting blood glucose levels below a predefined threshold (e.g., 55 ml/dL) and a user-defined threshold (e.g., 70 mg/dL). However, the diabetes management platform may also be able to detect trends/instances of near hypoglycemia without necessarily triggering an alert. For example, the diabetes management platform may detect that a subject consistently has a low blood glucose level (e.g., 75 mg/dL) in the early morning hours (e.g., around 3:00 AM). Although the diabetes management platform may not generate an alert specifying a hypoglycemic event occurred, the diabetes management platform may notify a health coach of such behavior.

FIG. 9 depicts an example of a visualization that includes two annotations corresponding to unlogged meals, two annotations corresponding to late evening meals, one annotation corresponding to an instance of poor glycemic recovery, and one annotation corresponding to a sensor dropout. Each annotation (also referred to as a "label," a "tag," or a "classification") is associated with a corresponding time interval, whose duration is defined by the at least one pair of adjacent minima used to define the excursion. In some instances, a glycemic event may be defined by multiple excursions. Here, for example, a single annotation is used to represent the unlogged meal that occurred around 4:30 PM. Annotations may also partially or entirely overlap one another. Here, for example, the annotation corresponding to the instance of poor glycemic recovery covers the same time interval as one of the annotations corresponding an unlogged meal.

Generally, sensor dropouts correspond to time intervals in which no physiological data has been acquired by the diabetes management platform. For example, physiological data may not be generated when the glucose monitoring device is replaced (e.g., on a weekly basis), the glucose monitoring device is dislodged (e.g., comes loose from the skin due to poor placement, loose tape, etc.), etc. As another example, physiological data may not be available if the communication channel between the glucose monitoring device and the computing device on which the diabetes management platform resides is disrupted. In such scenarios, the missing physiological data may not backfill if the glucose monitoring device is configured to stream physiological data to the computing device in real time.

As shown in FIG. 9, the visualization may also depict the glycemic range recommended by the ADA. Here, the recommended glycemic range of 80 mg/dL to 180 mg/dL is highlighted gray. However, the upper threshold (i.e., 180 mg/dL) and the lower threshold (i.e., 80 mg/dL) could also be depicted using horizontal lines (e.g., solid, dashed, or dotted lines).

Additionally or alternatively, other glycemic ranges may be depicted in a visualization. For example, a subject whose blood glucose level is being monitored may be associated with a healthcare regimen that is intended to guide the subject toward a healthier glycemic range. In such embodiments, the glycemic range depicted in the visualization may change over time. Thus, the glycemic range may be 120-220 mg/dl during a first time interval, 100-200 mg/dl during a second time interval, etc. Gradual shifts in the glycemic range can facilitate improvement in the glycemic health state of the subject in a manner more susceptible to behavior change (e.g., because the subject can readily examine their blood glucose level with respect to the changing glycemic range).

Annotations of different types may be arranged along separate tracks positioned beneath the glucose trace. The separate tracks enable the diabetes management platform to depict multiple annotations that are easily distinguishable from one another, yet still temporally aligned. Thus, the separate tracks enable the diabetes management platform to easily classify a time interval as being indicative of multiple glycemic events (and thus multiple annotations). Here, for example, the time interval from 4-9 PM is associated with an annotation corresponding to an instance of poor glycemic recovery and an annotation corresponding to an unlogged meal. Annotations of different types may also be visually distinguishable from one another. For example, in some embodiments each type of annotation is associated with a different color, while in other embodiments each type of annotation is associated with a different line type (e.g., solid, dashed, dotted, etc.).

In some embodiments, annotations are also used to identify physiological data values that require further examination/analysis. For example, if a subject sleeps on a glucose monitoring device, then the data values generated by the glucose monitoring device may be artificially low due to poor readings. Because the diabetes management platform can readily determine that these low data values are not indicative of the true blood glucose level (e.g., by comparing to previous nights or monitoring a trend in the blood glucose level throughout the day), the diabetes management platform can identify the corresponding time interval as being a candidate for further analysis.

Figure 10:
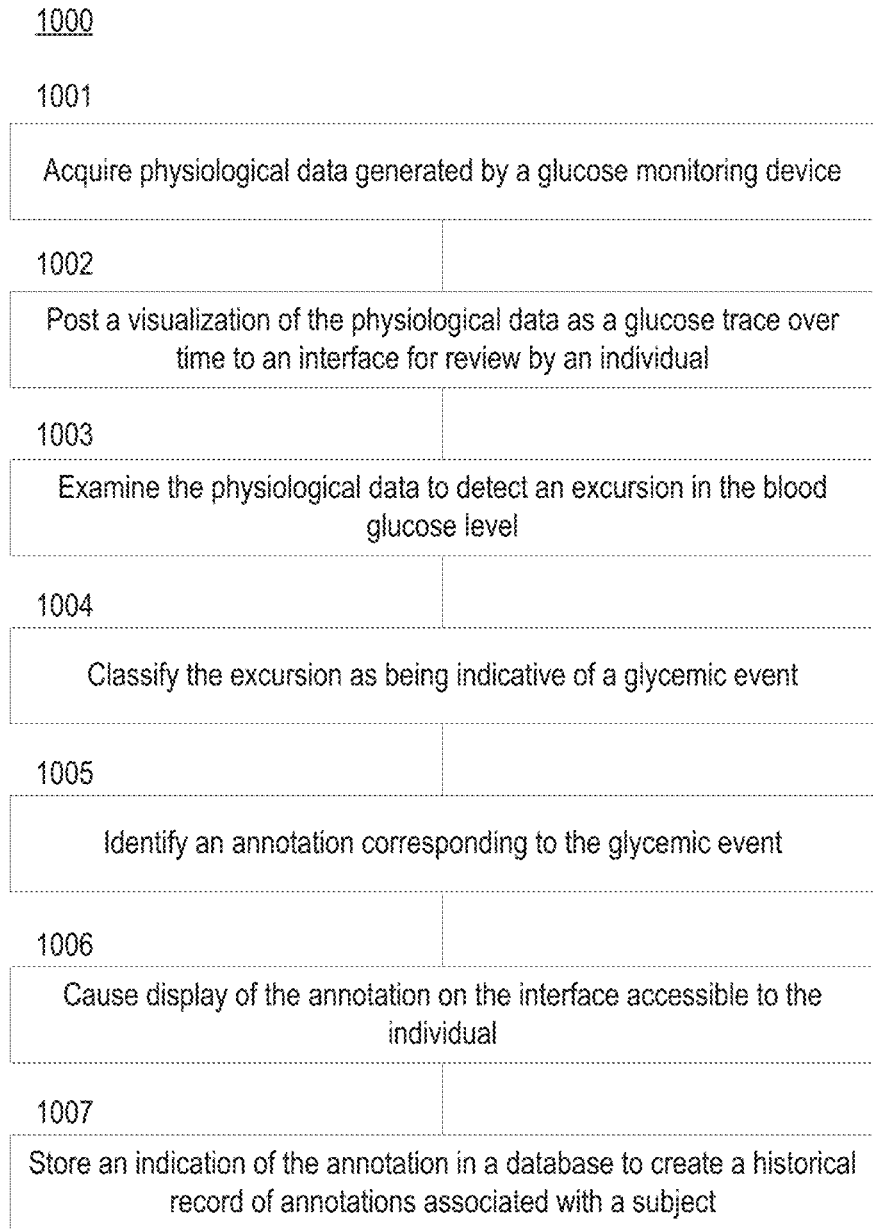
FIG. 10 depicts a flow diagram of a process for discovering signal features in physiological data specifying the blood glucose level of a subject whose glycemic health state is being monitored.

FIG. 10 depicts a flow diagram of a process 1000 for discovering signal features in physiological data specifying the blood glucose level of a subject whose glycemic health state is being monitored. By examining these signal features, a diabetes management platform can classify excursions detected in the physiological data to facilitate the identification of a therapeutic behavior change to be performed by the subject to improve the glycemic health state.

Initially, a diabetes management platform acquires physiological data (step 1001). Generally, the physiological data includes a series of static measurements of the blood glucose level of the subject. Thus, the physiological data may include discrete, digitally represented values in a temporal order that are indicative of time-varying glucose concentration as sampled on a periodic or ad hoc basis. In some embodiments, the physiological data also includes imputed measurements generated by the diabetes management platform (e.g., based on the series of static measurements).

The diabetes management platform can then post a visualization of the physiological data as a glucose trace over time to an interface for review by an individual (step 1002). In some embodiments the individual is a person with diabetes, while in other embodiments the individual is interested in examining physiological data associated with some other person. Thus, the individual may be a health coach such as a medical professional (e.g., a physician or nurse), a diabetic health counselor, a family member, etc. FIG. 9 depicts an example of a glucose trace that is based on explicit measurements generated by a continuous glucose monitor. However, a glucose trace could be based on explicit measurements, imputed measurements, or any combination thereof.

The diabetes management platform may also examine the physiological data to detect an excursion in the blood glucose level of the subject (step 1003). By parsing the physiological data, the diabetes management platform can detect a signal feature defined by one or more data values. Examples of signal features include the minimum blood glucose value, the maximum blood glucose value (also referred to as the "peak blood glucose value"), the total area beneath the peak blood glucose value (i.e., an integral of a glucose trace over the duration of the peak blood glucose value), a recovery rate following the peak blood glucose value, a time characteristic of the minimum or peak blood glucose values, etc. Thus, while some excursions may be defined by blood glucose level variations exceeding a specified amount, other excursions may be based on the magnitude of a single data value (e.g., in the case of the minimum and peak blood glucose values).

Several different techniques can be employed for detecting excursions in the blood glucose level of the subject. In some embodiments, the diabetes management platform detects an excursion that exceeds a specific threshold, selects a time interval that includes the excursion, and classifies, in response to selecting the time interval, the data value(s) defining the excursion as being indicative of a glycemic event. In other embodiments, the diabetes management platform segments the physiological data into multiple time intervals, classifies each time interval of the multiple time intervals based on the presence of any glycemic events, merges consecutive time intervals having the same classification, and identifies, from both the merged and unmerged time intervals, a time interval corresponding to a certain glycemic event. Accordingly, the multiple time intervals examined by the diabetes management time intervals may include both merged and unmerged time intervals (e.g., consecutive time intervals having the same classification are a subset of the multiple time intervals). Thus, the time interval under consideration may be a single time interval or a combined time interval formed from more than one of the multiple time intervals.

The diabetes management platform can then classify the excursion as being indicative of a glycemic event (step 1004). The term "glycemic event" broadly refers to any event that affects the blood glucose level. Examples of such events include the performance of an exercise activity, consumption of a foodstuff, administration of a medication, etc. Thus, the diabetes management platform may determine that an upward variation in the blood glucose level exceeding a certain amount likely corresponds to consumption of a foodstuff. Similarly, the diabetes management platform may determine that a downward variation in the blood glucose level exceeding a certain amount likely correspond to administration of a medication. In some embodiments, the diabetes management platform can detect characteristic(s) of the glycemic event based on feature(s) of the excursion. For example, if the upward variation in the blood glucose level exceeds a certain threshold, then the diabetes management platform may determine that the subject likely consumed a large meal or a meal high in carbohydrates. Examples of such excursion features include the total variation in the blood glucose level, duration of the excursion, maximum/minimum values, etc.

The diabetes management platform can also identify an annotation corresponding to the glycemic event (step 1005). For example, responsive to classifying the excursion as being indicative of a glycemic event, the diabetes management platform may designate an annotation for a target time period based on the glycemic event. In some embodiments, the target time period is the same as the time interval over which the signal feature is present. In other embodiments, the target time period is a subset of the time interval over which the signal feature is present. Said another way, the time interval may be a superset of the target time period. For example, the time interval may include an onset period preceding the annotated glycemic event and/or a tail period following the annotated glycemic event.

The diabetes management platform can then cause display of the annotation on the interface for review by the individual (step 1006). As shown in FIG. 9, the diabetes management platform may represent the annotation as a horizontal line arranged beneath a corresponding window of physiological data represented as a glucose trace. The glucose trace and the annotation can be aligned with respect to a common time axis, thereby visually alerting the individual of potential changes in the glycemic health state of the subject.

The diabetes management platform will often characterize continuous windows of physiological data with different annotation(s). As shown in FIG. 9, a visualization can include multiple annotations. Moreover, because an excursion may be indicative of multiple types of glycemic events, the diabetes management platform may overlay multiple annotations on top of one another (e.g., by arranging each annotation along a separate track beneath the glucose trace). Visual presentation of these annotations can facilitate the discovery of the glycemic health state of the subject, the recommendation of a therapeutic behavior change for improving the glycemic health state, the identification of comparable subjects and/or glycemic events, etc.

In some embodiments, the diabetes management platform further stores an indication of the annotation in a database to create a historical record of annotations associated with the subject (step 1007). Because each annotation is associated with a glycemic event, the historical record of annotations can also represent a historical record of glycemic events experienced by the subject. More specifically, the diabetes management platform can configure a subject profile in the database to specify that the glycemic event occurred at a certain time. Thus, the subject profile can include an entry for each glycemic event, a time interval during which the glycemic event occurred, etc. In some embodiments the time interval is dynamically generated (e.g., by identifying a start time corresponding to initiation of the excursion and an end time corresponding to conclusion of the excursion), while in other embodiments the time interval is selected from a predetermined list (e.g., by determining whether the glycemic event occurred during the morning, afternoon, evening, or night).

When the annotations are stored in the database, the diabetes management platform can perform various operations. For example, the diabetes management platform may receive input indicative of a request to identify similar instance(s). Thus, a health coach may ask to see instances where the subject experienced a physiological response to a meal, hypoglycemia, a blood glucose level exceeding 100 mg/dL during the night, a sensor dropout, etc. Moreover, the diabetes management platform may perform browsing/filtering of the historical record of annotations. Thus, a health coach may ask to see instances where the subject concurrently experienced two different glycemic events. These features are particularly useful for health coaches who are responsible for reviewing large sets of physiological data (e.g., for hundreds of subjects or over hundreds of days).

In some embodiments, some of these steps are not performed. For example, the diabetes management platform may not post a visualization of the physiological data to the interface or cause display of an annotation on the interface. Instead, the diabetes management platform may simply detect excursions in the physiological data, classify each excursion as being indicative of a glycemic event, and then create a historical record of the glycemic events experienced by the subject over time.

Other steps may also be included in some embodiments. For example, the diabetes management platform may perform an analytic process on physiological data to detect whether there are any time intervals in which the blood glucose measurements are rarely taken. Such action may be performed selectively. For instance, the diabetes management platform may only perform the analytic process responsive to discovering the physiological data was generated by a blood glucose meter that generates blood glucose measurements on an ad hoc basis. An annotation may be generated to identify these time intervals with sporadic coverage. Other examples of analytic processes include prioritizing recommendations provided for improving the glycemic health state of the subject, examining glucose-related metrics critical in guiding diabetes management in a personalized manner, posting certain glucose-related metrics and/or visualizations to an interface for review by the subject or a health coach, etc.

Managing Meal Excursions in Physiological Data

As noted above, individuals with diabetes can benefit from gaining a better understanding of how their blood glucose level fluctuates due to the consumption of meals. However, it can be difficult to understand which meals have the most significant impact on blood glucose level measurements, which represent a technical signal indicative of the diabetes disease state. Meals represent one example of a glycemic event whose impact has proven to be difficult to consistently and accurately present. The term "meal" refers to any event that involves the consumption of one or more foodstuffs.

To better understand the impact that meals have on the blood glucose level of an individual, a diabetes management platform can utilize information regarding meals consumed by the individual to manage the diabetes disease state in a personalized manner. More specifically, by acquiring data regarding the meals consumed by the individual, the diabetes management platform can consistently and properly attribute excursions in the blood glucose level to meals. Such action allows the relationship between meals and the glycemic health state to be better understood. As noted above, the meal data can include image(s) of the meals and/or information regarding the meals.

Figure 11:
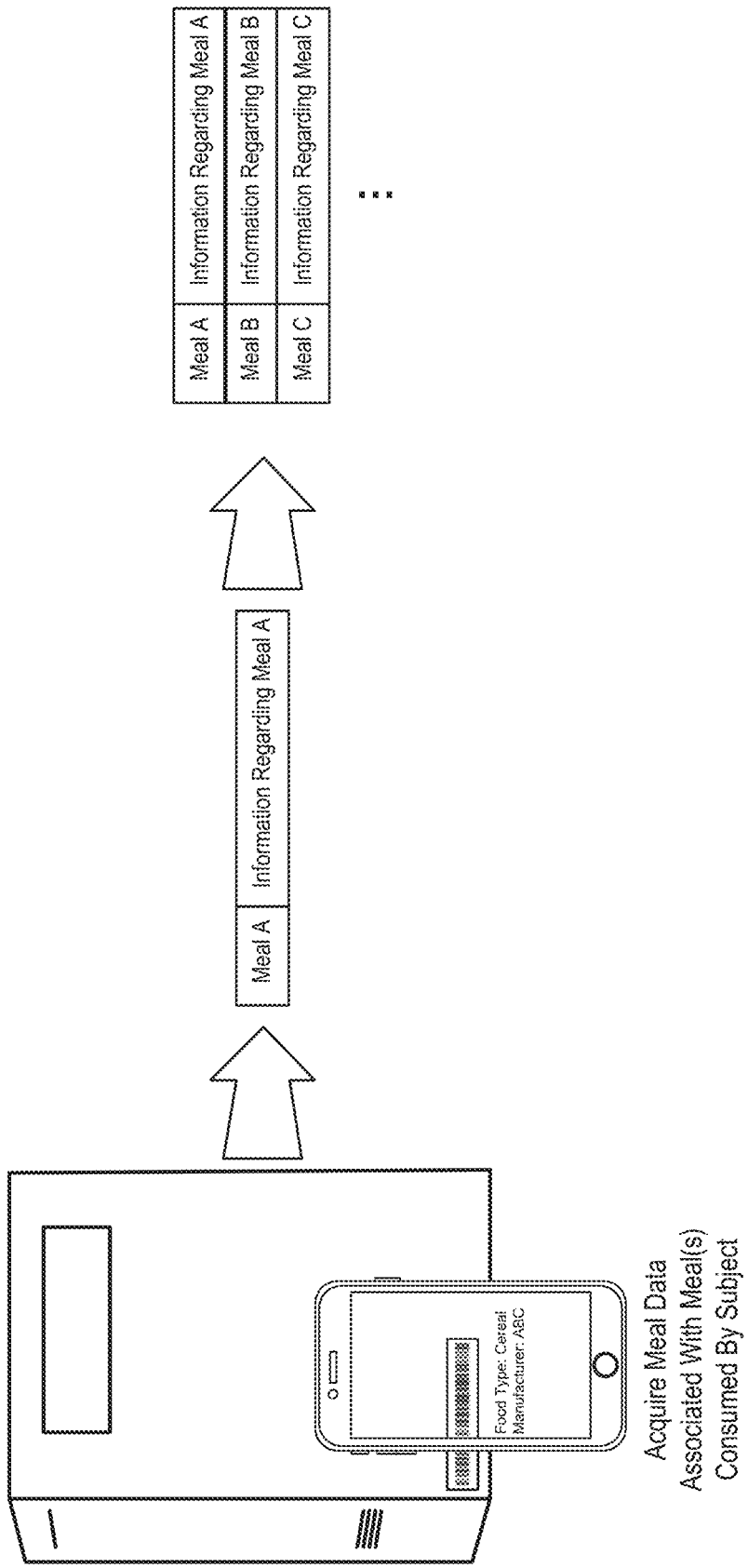
FIG. 11 includes a generalized illustration of an example of a process in which meal data is acquired by a diabetes management platform.

FIG. 11 includes a generalized illustration of an example of a process in which meal data is acquired by a diabetes management platform. The meal data is associated with meals consumed by a subject whose glycemic health state is to be monitored. However, meals can be reported by the subject in several different ways.

In some embodiments, the subject is permitted to capture images of codes associated with foodstuffs. In FIG. 11, for example, the subject has scanned a code affixed to the packaging of a foodstuff. A code can include machine-readable elements, human-readable elements, and/or structural elements. Machine-readable elements (e.g., bar codes and Quick Response (QR) codes) are designed to be interpreted by a computing device. Machine-readable elements can include extractable information, such as foodstuff type, foodstuff manufacturer, etc. Human-readable elements (e.g., text and images) may be co-located with the machine-readable elements and identified using various optical character recognition (OCR) techniques. Structural elements (e.g., emblems, horizontal lines, and solid bars) may also be used to identify a foodstuff from a code. The diabetes management platform may be able to extract information about a meal from a code. For example, upon determining that the subject has captured an image of a code affixed to a box of cereal, the diabetes management platform may infer that the subject consumed one serving of cereal.

In other embodiments, the subject is permitted to capture images of the foodstuff(s) included in a meal. In such embodiments, the diabetes management platform may be configured to automatically identify recognizable features of the foodstuffs. The diabetes management platform may apply image processing algorithm(s) to identify shapes and/or colors that are indicative of certain foodstuffs (e.g., green spheres for peas, orange cylinders for carrots, etc.). For example, the diabetes management platform may perform image segmentation (e.g., thresholding methods such as Otsu's method, or color-based segmentation such as K-means clustering) on individual images to isolate regions/objects of interest. These images may be static images or individual frames of a live video feed.

In other embodiments, the subject provides information regarding the meal before, during, or after consuming a meal. For example, the subject may populate the fields of a form accessible on a computing device. The subject may specify the foodstuff(s) included in the meal, the location of the meal, the time of the meal, the meal type (e.g., whether the meal corresponds to breakfast, lunch, dinner, or a snack), which individual(s) were present, etc.

Those skilled in the art will recognize that these options for reporting meals are not mutually exclusive. For example, a subject may capture an image of a meal using a computing device and provide information regarding the meal through an interface accessible on the computing device.

Data regarding the meals consumed by the subject can be acquired, derived, or created based on the information provided by the subject regardless of its form. For example, if the subject captures an image of a given meal, the diabetes management platform may create meal data based on an analysis of the image. As shown in FIG. 11, the diabetes management platform can populate a database record with this meal data. In some embodiments, the database record is stored within a database associated with a user profile for the subject. Accordingly, the diabetes management platform may maintain a list of meals consumed by the subject (and information regarding those meals) over time.

Figure 12:
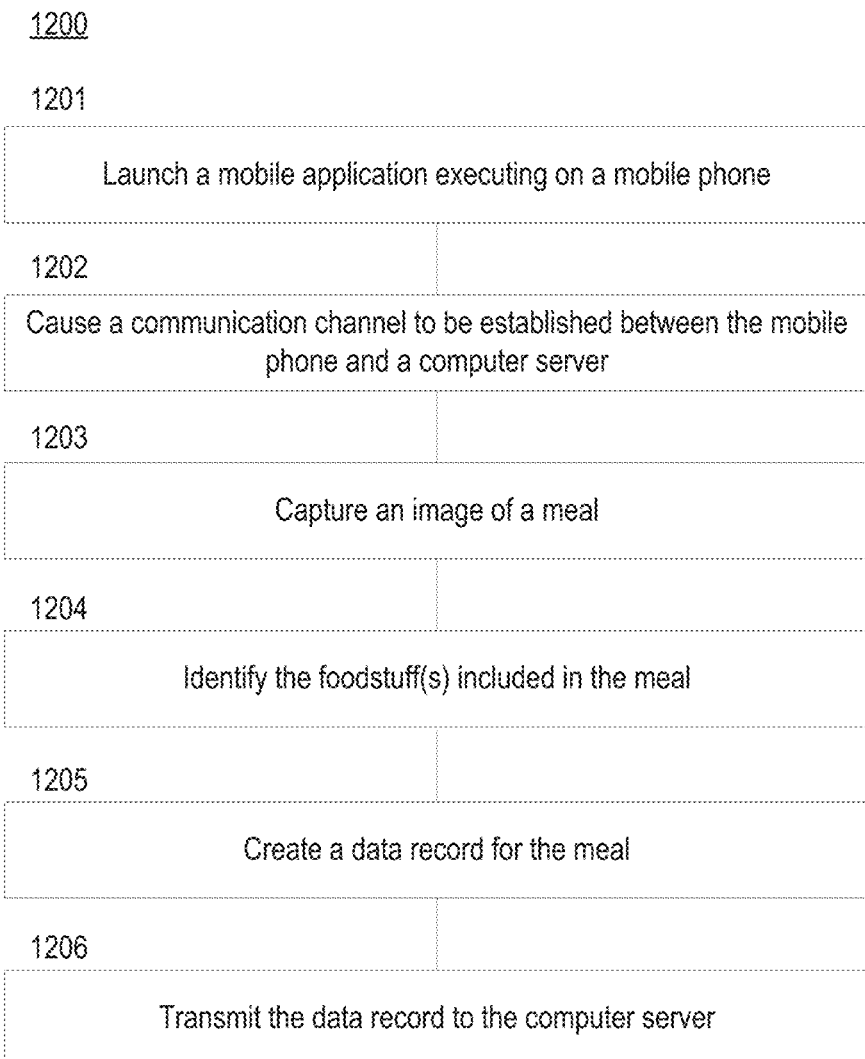
FIG. 12 depicts a flow diagram of a process for generating meal data based on information that has been discovered through an analysis of an image of a meal.

FIG. 12 depicts a flow diagram of a process 1200 for generating meal data based on information that has been discovered through an analysis of an image of a meal. Here, the process 1200 is described as being performed by a diabetes management platform implemented as a mobile application that is executed by a mobile phone associated with a subject, while the diabetes management platform is supported by a back-end service executed by a computer server. The back-end service may be responsible for supporting the diabetes management platform. As noted above, however, that the diabetes management platform could instead reside on the computer server.

Initially, an individual launches the diabetes management platform that is executing on the mobile phone (step 1201). The diabetes management platform can then cause a communication channel to be established between the mobile phone and a computer server (step 1202). The computer server may be part of a network-connected server system that supports various functionalities of the diabetes management platform.

The individual can then capture an image of a meal using the mobile phone (step 1203). In some embodiments, the image is captured while the diabetes management platform is executing on the mobile phone. For example, upon selecting a digital element accessible on an interface generated by the diabetes management platform, the subject may be permitted to capture the image of the meal. In other embodiments, the subject may opt to upload an image of a past meal to the diabetes management platform. For example, upon selecting a digital element accessible on an interface generated by the diabetes management platform, the subject may be permitted to browse a library of images maintained on the mobile phone and then select an image to be uploaded to the diabetes management platform.

In some embodiments, the diabetes management platform identifies at least some of the foodstuffs included in the meal (step 1204). For example, the diabetes management platform may perform image processing to automatically identify shapes, colors, or combinations thereof that are indicative of certain foodstuffs. Additionally or alternatively, the diabetes management platform may receive input indicative of a specification of the foodstuff(s) included in the meal.

Thereafter, the diabetes management platform can create a data record for the meal (step 1205). The data record may include the image of the meal, as well as information associated with the meal. This information may be provided by the individual. For example, the individual may provide this information through an interface accessible on the mobile phone. Examples of such information include the foodstuff(s) included in the meal, the location of the meal, the time of the meal, the meal type, etc. In some embodiments, at least some of this information is automatically derived without requiring any input from the individual. For example, the diabetes management platform may establish the time of a meal by extracting a timestamp from metadata associated with the image of the meal. As another example, the diabetes management platform may infer the location of the meal based on the location of the mobile phone (e.g., as determined by its operating system).

In some embodiments, the diabetes management platform transmits the data record to the computer server (step 1206). Upon receiving the data record, a back-end service responsible for supporting the diabetes management platform may store the data record in a profile associated with the individual. Such action may also be performed by the diabetes management platform. In such instances, the profile may be hosted entirely on the mobile phone (e.g., for privacy purposes). As data records for meals are created over time, the back-end service and/or the diabetes management platform may maintain a historical record of meals consumed by the individual.

FIG. 13 depicts a flow diagram of a process 1300 for matching excursions discovered in physiological data to meals consumed by an individual. Such action enables a diabetes management platform to better understand how certain meals affect the glycemic health state of the individual, both in the short term and the long term, thereby enabling the diabetes management platform (or a health coach) to provide more suitable recommendations for improving the glycemic health state.

Initially, a diabetes management platform can receive a series of blood glucose values associated with an individual (step 1301). The series of blood glucose values (also referred to as "physiological data") can include explicit data values generated by a glucose monitoring device and/or implicit data values generated by the diabetes management platform. For example, the physiological data may include a series of explicit data values corresponding to a first interval of time and a series of imputed data values corresponding to a second interval of time following the first interval of time.

The diabetes management platform can then examine the series of blood glucose values to detect an excursion in the blood glucose level (step 1302). For example, the diabetes management platform may parse the series of data values to discover an excursion defined by a pair of dynamically-determined, semi-global minima values and a peak value. As another example, the diabetes management platform may apply a machine-learnt model that considers the series of data values as input. Step 1302 of process 1300 may be substantially similar to step 1003 of process 1000.

Thereafter, the diabetes management platform can acquire meal data associated with meal(s) consumed by the individual (step 1303). As noted above, the meal data may be provided by the individual, derived on behalf of the individual, or any combination thereof. For example, the meal data may include image(s) of meals that have been uploaded by the individual. As another example, the meal data may include information provided by the individual regarding meals. As another example, the diabetes management platform may automatically establish a characteristic of a meal (e.g., its time, foodstuffs, or participants) based on an analysis of the image or metadata associated with the image.

The diabetes management platform can then match the excursion discovered in the physiological data to a particular meal reported by the individual (step 1304). For example, the diabetes management platform may parse the meal data to establish a meal time for each meal reported by the individual, identify an excursion time corresponding to the excursion, and then determine that the excursion time follows a particular meal time corresponding to the particular meal within a predetermined amount of time. The predetermined amount of time may be based on a characteristic of the individual. Thus, the delay between meals and the physiological responses to those meals may differ from person to person. To match excursions to meals, the diabetes management platform may apply a matching algorithm that is personalized for each individual by recognizing the total possible range of delays, as well as the expected delay, experienced by those individuals in the past.

In some embodiments, the diabetes management platform is configured to classify each excursion in the physiological data that corresponds to a meal as being indicative of a negative event likely to negatively affect the glycemic health of the individual, a positive event likely to positively affect the glycemic health of the individual, or a neutral event that is unlikely to affect the glycemic health of the individual. Here, for example, the diabetes management platform has determined that the excursion corresponds to a negative event. Said another way, the diabetes management platform has determined that the physiological reaction represented by the excursion occurred in response to a meal that negatively affected the glycemic health state of the individual (step 1305).

In such embodiments, the diabetes management platform may identify the excursion as being representative of a negative event (step 1306). Such action enables the diabetes management platform to readily identify those meals that should be avoided in the future, as well as identify those meals that represent a better alternative from a glycemic health perspective. For example, the diabetes management platform may be able to identify similar past meals by examining physiological data associated with a past interval of time to detect similar excursions. As another example, the diabetes management platform may be able to predict similar future meals by examining physiological data associated with a future interval of time to detect similar excursions. Generally, physiological data associated with past intervals of time will include at least some explicit data values, while physiological data associated with future intervals of time will be comprised entirely of imputed data values.

The diabetes management platform may also be able to predict similar future meals by examining other information. For example, the diabetes management platform may infer the location of the individual based on the location of a computing device (e.g., as determined by its operating system) associated with the individual. Upon determining that the individual is located proximate to the location of a past meal, the individual may generate a recommendation based on the past meal. For instance, the diabetes management platform may recommend that the individual avoid the past meal, select an alternatively meal or restaurant, etc.

FIG. 14 depicts a flow diagram of a process 1400 for determining whether to classify excursions as events that increase health risk. Said another way, by executing the process 1400, a diabetes management platform can determine whether a given excursion should be placed within an increased-risk group (also referred to as an "increased-risk bucket").

Initially, the diabetes management platform can acquire a series of labeled excursions corresponding to a series of glycemic events (step 1401). Each glycemic event can be labeled as a negative event (also referred to as a "bad event" or a "high-risk event") or a positive event (also referred to as a "good event"). "Bad events" are those glycemic events that have either negatively affected glycemic health or increased the risk/likelihood of experiencing a negative health outcome, while "good events" are those glycemic events that have positively affected glycemic health. These excursions may be hand-labeled by medical professionals, such as physicians or nurses.

The diabetes management platform can then train a supervised model with the series of labeled excursions (step 1402). After the supervised model has been trained, the supervised model can take blood glucose values as input and identify segments of time that correspond to excursions as output. Moreover, the supervised model may determine whether these excursions are "bad events" or "good events." Accordingly, the diabetes management platform can receive a series of blood glucose values associated with a subject (step 1403), and then apply the supervised model to the series of blood glucose values to identify and classify excursions (step 1404).

In some embodiments, the diabetes management platform is able to produce a summary of excursions, if any, that have been classified as being indicative of "bad events" (step 1405). The diabetes management platform may post the summary to an interface for review by an individual (step 1406). The individual may be the subject whose blood glucose level is being monitored or a health coach responsible for discouraging the subject from performing activities (e.g., eating meals) associated with excursions corresponding to "bad events."

In some embodiments, the diabetes management platform applies an unsupervised model to another series of excursions to produce one or more clusters (step 1407). Such action enables the diabetes management platform to cluster those excursions having a similar effect on the blood glucose level. This other series of excursions may include labeled excursions (e.g., excursions from the series described above with respect to step 1401), unlabeled excursions, or any combination thereof. Moreover, this other series of excursions may include excursions experienced by a single subject or a cohort of multiple subjects.

The diabetes management platform can also acquire images of meals that correspond to this other series of excursions (step 1408). The diabetes management platform may sort these images into one or more batches corresponding to the cluster(s) formed by the unsupervised model (step 1409). The diabetes management platform may analyze the image(s) in each batch to discover a meal preference of the subject(s), identify more appropriate recommendations for the subject(s), etc.

FIG. 15 depicts a flow diagram of a process 1500 for managing the glycemic health state of an individual in a personalized manner based on the meals consumed by the individual. Initially, a diabetes management platform can identify a series of historical meals consumed by an individual whose glycemic health state is to be monitored (step 1501). Generally, these meals are reported by the individual (e.g., by uploading images of the meals). However, as noted above, the diabetes management platform could automatically discover the occurrence of meals on behalf of the individual.

The diabetes management platform can then detect multiple excursions in a series of blood glucose values associated with the individual (step 1502). Step 1502 of process 1500 may be substantially similar to step 1302 of process 1300 and step 1003 of process 1000. The diabetes management platform can then match each excursion of the multiple excursions discovered in the series of blood glucose values to a corresponding historical meal in the series of historical meals (step 1503). Step 1503 of process 1500 may be substantially similar to step 1304 of process 1300.

In some embodiments, the diabetes management platform classifies, based on the corresponding excursion, each historical meal as being representative of a negative meal, a positive meal, or a neutral meal (step 1504). In other embodiments, the diabetes management platform classifies each historical meal as being representative of a negative meal or a positive meal. As noted above, negative meals are those meals that have negatively affected glycemic health, positive meals are those meals that have positively affected glycemic health, and neutral meals are those meals that have not had any medically significant impact on glycemic health.

The diabetes management platform can also identify a meal preference of the individual by examining the pixel data of images of the series of historical meals (step 1505). For example, the diabetes management platform may discover, by applying image processing algorithm(s), which meals are consumed most frequently, the cadence of certain meals, etc. Thereafter, the diabetes management platform may generate a meal recommendation based on the meal preference (step 1506), and then cause display of the meal recommendation to the individual. For example, the diabetes management platform may compare the meal preference to a first list of meals classified as being likely to negatively affect glycemic health and a second list of meals classified as being likely to positively affect glycemic health. If the meal preference matches the first list of meals, then the diabetes management platform may recommend that the individual consider a meal in the second list of meals or avoid the meal preference entirely. Thus, the diabetes management platform may automatically generate recommendations for meal substitutions upon discovering that the individual has eaten, or is likely to eat, a meal that increases health risk. In some embodiments, the first and second lists of meals are predetermined (e.g., specified by a medical professional). In other embodiments, the first and second lists of meals are dynamically altered over time as the diabetes management platform classifies additional meals reported by the individual. Thus, the first and second lists of meals may be personalized on an individual basis.

These steps may be performed in various sequences and combinations. For example, in some embodiments the diabetes management platform acquires meal data and physiological data simultaneously, while in other embodiments the diabetes management platform acquires the meal data before or after acquiring the physiological data.

Other steps may also be included in some embodiments. For example, the diabetes management platform may create a personalized profile for an individual whose glycemic health state is to be monitored. The personalized profile may specify one or more food groups that have been beneficial to the individual and/or one or more food groups that have been detrimental to the individual. These "good" food group(s) and "bad" food group(s) may be established by the diabetes management platform through an analysis of excursions in the blood glucose level caused by meals and images of those meals. These food groups may be defined by a health coach, defined by the diabetes management platform, defined by an algorithm designed to cluster images based on visual similarity, defined by an algorithm designed to cluster excursions based on physiological similarity, or defined by an algorithm designed to append classification labels to images of meals based on information regarding those meals.

Processing System

Figure 16:
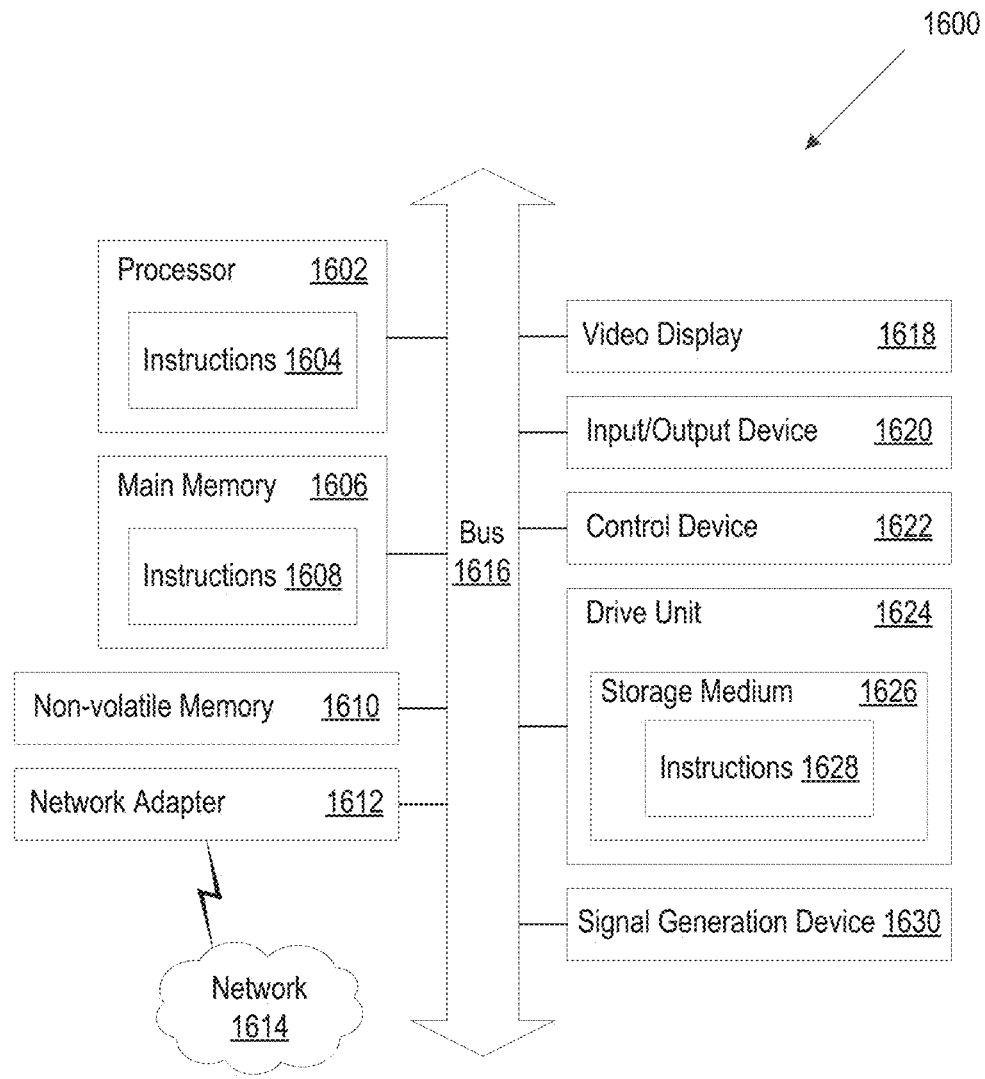
FIG. 16 is a block diagram illustrating an example of a processing system in which at least some operations described herein can be implemented.

FIG. 16 is a block diagram illustrating an example of a processing system 1600 in which at least some operations described herein can be implemented. For example, some components of the processing system 1600 may be hosted on a computing device that includes a diabetes management platform (e.g., diabetes management platform 102 of FIG. 1).

The processing system 1600 may include one or more central processing units ("processors") 1602, main memory 1606, non-volatile memory 1610, network adapter 1612 (e.g., network interface), video display 1618, input/output devices 1620, control device 1622 (e.g., keyboard and pointing devices), drive unit 1624 including a storage medium 1626, and signal generation device 1630 that are communicatively connected to a bus 1616. The bus 1616 is illustrated as an abstraction that represents one or more physical buses and/or point-to-point connections that are connected by appropriate bridges, adapters, or controllers. The bus 1616, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The processing system 1600 may share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the processing system 1600.

While the main memory 1606, non-volatile memory 1610, and storage medium 1626 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 1628. The term "machine-readable medium" and "storage medium" shall also be taken to include any medium that is capable of storing, encoding, or carrying a set of instructions for execution by the processing system 1600.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 1604, 1608, 1628) set at various times in various memory and storage devices in a computing device. When read and executed by the one or more processors 1602, the instruction(s) cause the processing system 1600 to perform operations to execute elements involving the various aspects of the disclosure.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 1610, floppy and other removable disks, hard disk drives, optical disks (e.g., Compact Disk Read-Only Memory (CD-ROMS), Digital Versatile Disks (DVDs)), and transmission-type media such as digital and analog communication links.

The network adapter 1612 enables the processing system 1600 to mediate data in a network 1614 with an entity that is external to the processing system 1600 through any communication protocol supported by the processing system 1600 and the external entity. The network adapter 1612 can include a network adaptor card, a wireless network interface card, a router, an access point, a wireless router, a switch, a multilayer switch, a protocol converter, a gateway, a bridge, bridge router, a hub, a digital media receiver, and/or a repeater.

The network adapter 1612 may include a firewall that governs and/or manages permission to access/proxy data in a computer network and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall may additionally manage and/or have access to an access control list that details permissions including the access and operation rights of an object by an individual, a machine, and/or an application, and the circumstances under which the permission rights stand.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or

Remarks

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. A method comprising:
   receiving, by a processor, a series of blood glucose values associated with an individual;
   identifying, by the processor in the series of blood glucose values, a pair of semi-global minima values occurring within a configurable interval of time with a peak value therebetween;
   measuring, by the processor, a magnitude between the pair of semi-global minima values and the peak value;
   determining, by the processor, that an excursion has occurred in the series of blood glucose values upon establishing that the magnitude crosses a specified threshold;
   correlating, by the processor, the excursion with a particular meal consumed by the individual by associating the pair of semi-global minima values and the peak value with an indicium of the particular meal in a data structure that is representative of a profile maintained for the individual;
   deriving, by the processor through an analysis of the data structure, a meal-related insight by establishing meals, if any, that increase a likelihood of experiencing an adverse health event; and
   presenting, by the processor via a communication interface, a recommendation to the individual that is based on the meal-related insight.

2. The method of claim 1, wherein the indicium is an image of the particular meal that is provided by the individual.

3. The method of claim 2, further comprising:
   posting, to the communication interface, information regarding the particular meal that is derived through analysis of the image.

4. The method of claim 1, wherein the series of blood glucose values includes estimated values, actual values, or any combination thereof.

5. The method of claim 1, further comprising:
   determining, based on the excursion, that consumption of the particular meal negatively affects a glycemic health state of the individual; and
   classifying the excursion as representative of a negative glycemic event.

6. The method of claim 1, wherein said identifying is accomplished by applying a machine-learnt model that considers the series of blood glucose values as input.

7. The method of claim 1, wherein over time, excursions are occurring at different times are correlated with indicia of different meals consumed by the individual to create a log from which the meal-related insight is derived.

8. The method of claim 1, further comprising:
   identifying, by the processor in a second series of blood glucose values that succeeds the series of blood glucose values, a second excursion that is defined by a second pair of semi-global minima values occurring within the configurable interval of time with a second peak value therebetween;
   determining, by the processor, that the second excursion is comparable to the excursion; and
   causing, by the processor via the communication interface, a recommendation for addressing the second excursion.

9. A non-transitory medium with instructions stored thereon that, when executed by a processor of a computing device, cause the computing device to perform operations comprising:
   obtaining a series of blood glucose values associated with an individual;
   identifying, in the series of blood glucose values, an excursion that is defined by a pair of semi-global minima values occurring within a configurable interval of time with a peak value therebetween;
   in response to said identifying,
      accessing multiple images that are associated with multiple meals consumed by the individual,
         wherein each image of the multiple images is associated with a corresponding meal of the multiple meals, and
      reviewing at least one of the multiple images that are generated within a predetermined temporal proximity of the excursion, so as to identify a particular image of a particular meal that is determined to have caused the excursion;
   correlating the excursion with the particular meal by associating the pair of semi-global minima values and the peak value with the particular image;

storing an indication of the correlation between the excursion and the particular meal in a data structure; and presenting, via a communication interface, information regarding the particular meal to encourage behavior change to improve a glycemic health state.

10. The non-transitory medium of claim 9, wherein the information comprises a summary of the excursion, so as to inform the individual of an impact of the particular meal on the glycemic health state.

11. The non-transitory medium of claim 9, wherein the information is derived through analysis of the particular image.

12. The non-transitory medium of claim 9, wherein said correlating comprises:

establishing a meal time for each meal of the multiple meals;

identifying an excursion time that corresponds to the excursion in the series of blood glucose values; and determining that the excursion time follows a particular meal time associated with the particular meal within a predetermined amount of time.

13. The non-transitory medium of claim 12, wherein each meal time is established by examining input received from the individual.

14. The non-transitory medium of claim 12, wherein each meal time is established by examining metadata associated with a corresponding image of the multiple images.

15. The non-transitory medium of claim 12, wherein the predetermined amount of time is based on a characteristic of the individual.

16. The non-transitory medium of claim 9, wherein the excursion is one of multiple excursions identified in the series of blood glucose values, and wherein said correlating is performed for each excursion of the multiple excursions, so as to associate variations in blood glucose that exceed a predetermined magnitude with images of meals consumed by the individual.

17. The non-transitory medium of claim 9, wherein said identifying comprises applying, to the series of blood glucose values, an algorithm that considers (i) a timescale parameter and (ii) a height parameter, and wherein when applied to the series of blood glucose values, the algorithm, identifies semi-global minima values in order of the timescale parameter by:

identifying all semi-global minima values that are lower than a preceding value and a succeeding value, pairing successive semi-global minima values to define excursions, and discarding excursions where a height of the excursion is less than the height parameter.

18. A method performed by a processor of a computing device, the method comprising:

acquiring a series of labeled excursions corresponding to a series of events, wherein each labeled excursion in the series of labeled excursions is defined by a pair of semi-global minima values occurring within a configurable interval of time with a peak value therebetween, and wherein each labeled excursion in the series of labeled excursions specifies whether a corresponding event in the series of events positively or negatively affected glycemic health;

providing the series of labeled excursions to an untrained supervised model as input, so as to produce a trained supervised model;

receiving a series of blood glucose values associated with an individual; and applying the trained supervised model to the series of blood glucose values, wherein said applying causes the trained supervised model to:

detect at least one excursion in the series of blood glucose values, and classify each detected excursion as being indicative of a positive event likely to positively affect glycemic health of the individual, or a negative event likely to negatively affect glycemic health of the individual.

19. The method of claim 18, further comprising:

posting a summary of excursions classified as being indicative of negative events to an interface that is accessible to a person responsible for monitoring glycemic health of the individual.

20. The method of claim 18, further comprising:

posting a summary of excursions classified as being indicative of negative events to an interface that is accessible to the individual, so as to inform the individual of an actual impact or an estimated impact on glycemic health.

21. The method of claim 18, wherein the series of events involve a population of multiple individuals.

22. The method of claim 18, further comprising:

applying an unsupervised model to the at least one detected excursion to produce at least one cluster, wherein each cluster includes one or more excursions determined to have a similar effect on glycemic health of the individual.

23. The method of claim 22, further comprising:

acquiring an image for each detected excursion in the series of blood glucose values, so as to acquire at least one image; and sorting the at least one image into at least one batch, wherein each batch of the at least one batch is associated with a corresponding cluster of the at least one cluster, and wherein each batch of the at least one batch includes one or more images corresponding to the one or more excursions in the corresponding cluster.

24. The method of claim 23, wherein each image of the at least one image is associated with a different meal consumed by the individual, and wherein the method further comprises:

creating a personalized meal profile for the individual based on an analysis of the at least one image.

25. The method of claim 23, wherein each image of the at least one image is associated with a different meal consumed by the individual, and wherein the method further comprises:

generating a meal recommendation for the individual based on an analysis of the at least one image; and posting the meal recommendation to an interface that is accessible to the individual.

* * * * *